(12) United States Patent
Pestova et al.

(10) Patent No.: US 9,752,196 B2
(45) Date of Patent: Sep. 5, 2017

(54) DETECTION OF CHROMOSOMAL ABNORMALITIES ASSOCIATED WITH PROGNOSIS OF NON SMALL CELL LUNG CANCER

(75) Inventors: Ekaterina Pestova, Glenview, IL (US); Mona Stein Legator, Evanston, IL (US); Xin Lu, Libertyville, IL (US); Dimitri Semizarov, Chicago, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

(21) Appl. No.: 13/499,850

(22) PCT Filed: Oct. 25, 2010

(86) PCT No.: PCT/US2010/053953
§ 371 (c)(1),
(2), (4) Date: Jun. 25, 2012

(87) PCT Pub. No.: WO2011/056505
PCT Pub. Date: May 12, 2011

(65) Prior Publication Data
US 2012/0264635 A1    Oct. 18, 2012

Related U.S. Application Data

(60) Provisional application No. 61/254,968, filed on Oct. 26, 2009, provisional application No. 61/254,955, filed on Oct. 26, 2009.

(51) Int. Cl.
*C12Q 1/68* (2006.01)

(52) U.S. Cl.
CPC ......... *C12Q 1/6886* (2013.01); *C12Q 1/6841* (2013.01); *C12Q 2600/118* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

| | | |
|---|---|---|
| 5,143,854 A | 9/1992 | Pirrung |
| 5,491,224 A | 2/1996 | Bittner |
| 2003/0022257 A1 | 1/2003 | Macina et al. |
| 2006/0063194 A1 | 3/2006 | Morrison et al. |
| 2006/0078885 A1 | 4/2006 | Katz et al. |
| 2008/0160533 A1 | 7/2008 | Hayden |
| 2008/0220424 A1 | 9/2008 | Haber et al. |
| 2010/0120027 A1* | 5/2010 | Morrison et al. ............... 435/6 |
| 2010/0291569 A1 | 11/2010 | Hayden |

FOREIGN PATENT DOCUMENTS

| | | |
|---|---|---|
| WO | WO 93/18186 | 9/1993 |
| WO | WO 96/17958 | 6/1996 |
| WO | WO 96/39154 | 12/1996 |
| WO | WO 97/03211 | 1/1997 |
| WO | WO 2005/117553 | 12/2005 |
| WO | WO 2006/056766 | 6/2006 |
| WO | WO 2006/104912 | 10/2006 |
| WO | 2007055553 A1 | 5/2007 |
| WO | WO 2008095049 A2 * | 8/2008 |
| WO | WO 2009/073425 | 6/2009 |
| WO | 2009129154 A1 | 10/2009 |
| WO | 2010121380 A1 | 10/2010 |
| WO | WO 2011/056505 | 5/2011 |

OTHER PUBLICATIONS

Banerji, M.A. et al., "Coronary heart disease risk factor profiles in black patients with non-insulin-dependent diabetes mellitus: paradox patterns," Am. J. Med. (1991) 91:51-58.
Birchmeier, C. et al., "MET, metastasis, motility and more," Nature Rev. Mol. Cell Biol. (2003) 4:915-925.
Campbell et al., 10.1073/pnas.0605296103 supporting information, accessed from http://www.pnas.org/content/103/45/16834/suppl/DC1[Sep. 17, 2012 5:13:52 PM], 139 pages.
Campbell et al., "A genetic variant that disrupts MET transcription is associated with autism," Proc. Natl. Acad. Sci. (2006) 103(45):16834-16839.
Dietrich, S. et al., "Role of C-MET in upper aerodigestive malignancies—from biology to novel therapies," J. Environ. Pathol. Toxicol. Oncol. (2005) 24(3):149-162.
Fodor, S.P.A. et al., "Light-directed, spatially addressable parallel chemical synthesis," Science (1991) 767-773.
Garnis, C. et al., "Involvement of multiple developmental genes on chromosome 1p in lung tumorigenesis," Hum. Mol. Genet. (2005) 14(4):475-482.
Halling, K. et al., "Fluorescence in situ hybridization in diagnostic cytology," Hum. Path. (2007) 38:1134-1144.
Kim, I.J. et al., "A novel germline mutation in the MET extracellular domain in a Korean patient with the diffuse type of familial gastric cancer," J. Med. Genet. (2003) 40:e97, 4 pages.
Kong-Beltran, M. et al., "Somatic mutations lead to an oncogenic deletion of MET in lung cancer," Cancer Res. (2006) 66(1):283-289.
Ma, P. et al., "Functional expression and mutations of c-Met and its therapeutic inhibition with SU11274 and small interfering RNA in non-small cell lung cancer," Cancer Res. (2005) 65:1479-1488.
Ma, P.C. et al., "C-MET: structure, functions and potential for therapeutic inhibition," Cancer Metastasis (2003) 22(4):309-325.
Mata, "A hexameric phosphorothioate oligonucleotide telomerase inhibitor arrests growth of Burkitt's lymphoma cells in vitro and in vivo," Toxicol. Apply. Pharmacol. (1997) 144:189-197.

(Continued)

*Primary Examiner* — Kaijiang Zhang
(74) *Attorney, Agent, or Firm* — Lisa V. Mueller; Michael Best & Friedrich LLP

(57) ABSTRACT

The methods and compositions described herein address the need for a diagnostic method that can be provided to patients with early stage lung cancer, especially non-small cell lung cancer (NSCLC), to determine whether the patient is at increased risk of poor disease outcome. The methods and compositions thus allow for more informed treatment decisions for the early stage lung cancer patient.

11 Claims, 9 Drawing Sheets

(56) References Cited

OTHER PUBLICATIONS

Matsuzaki, H. et al., "Genotyping over 100,000 SNPs on a pair of oligonucleotide arrays," Nat. methods (2004) 1:109-111.
Maulik, G. et al., "Role of the hepatocyte growth factor receptor, c-MET, in oncogenesis and potential for therapeutic inhibition," Cytokine and Growth Factor Reviews (2002) 13(1):41-59.
Milligan, J., "Current concepts in antisense drug design," Med. Chem. (1993) 36:1923-1937.
Morrison, L. et al., "Labeling fluorescence in situ hybridization probes for genomic targets," in Molecular Cytogenetics: Protocols and Applications (2002), Humana Press, Y.S. Fan, editor, Chapter 2, pp. 21-40.
NCBI dbSNP database record having rs185830, accessed from http://www.ncbi.nlm.nih.gov/projects/SNP/snp_ref.cgi?rs=185830[Sep. 12, 2012 12:19:09 PM] 2 pages.
Samstag, W., "Synthesis and properties of new antisense oligodeoxynucleotides containing benzylphosphanate linkages," Antisense Nucl. Acid. Drug Dev. (1996) 6:153-156.
Singhal, S. et al., "Prognostic implications of cell cycle, apoptosis, and angiogenesis biomarkers in non-small cell lung cancer: a review," Clin Cancer Res. (2005) 11:3974-3986.
Smolen, G. et al., "Amplification of MET may identify and subset of cancers with extreme sensitivity to the selective tyrosine kinase inhibitor PHA-665752," Proc. Nat. Acad. Sci. (2006) 103(7):2316-2321.
Strauss-Soukup, "Effects of neutralization pattern and sterochemistry on DNA bending by methylphosphonate substitutions," Biochem. (1997) 36:8692-8698.
Tai, A.L.S. et al., "Recurrent chromosomal imbalances in nonsmall cell lung carcinoma," Cancer (2004) 100(9):1918-1927.
United States Patent Office Action for U.S. Appl. No. 11/998,321 dated Aug. 12, 2009 (11 pages).
United States Patent Office Action for U.S. Appl. No. 12/744,458 dated Sep. 24, 2012 (17 pages).
European Patent Office Action for Application No. 08857918.0 dated Jan. 18, 2012 (4 pages).
International Search Report for Application No. PCT/US2008/084462 dated May 8, 2009 (4 pages).
International Search Report for Application No. PCT/US2010/53953 dated Feb. 15, 2011 (4 pages).
Written Opinion for Application No. PCT/US2008/084462 dated May 8, 2009 (6 pages).
Written Opinion for Application No. PCT/US2010/53953 dated Feb. 15, 2011 (7 pages).
Broet P., et al., "Prediction of Clinical Outcome in Multiple Lung Cancer Cohorts by Integrative Genomics: Implications for Chemotherapy Selection," Cancer Research, 2009, vol. 69 (3), pp. 1055-1062.
Fong KM., et al., "Mycl Genotypes and Loss of Heterozygosity in Non-small-cell Lung Cancer.," British Journal of Cancer, 1996, vol. 74 (12), pp. 1975-1978.
Gallegos Ruiz M.I., et al., "Integration of Gene Dosage and Gene Expression in Non-small Cell Lung Cancer, Identification of HSP90 as Potential Target.," Plos One, 2008, vol. 3 (3), pp. E1722.
Gasparian A.V., et al., "Allelic Imbalance and Instability of Microsatellite Loci on Chromosome 1p in Human Non-small-cell Lung Cancer.," British Journal of Cancer, 1998, vol. 77 (10), pp. 1604-1611.
Michelland S., et al., "Comparison of Chromosomal Imbalances in Neuroendocrine and Non-small-cell Lung Carcinomas.," Cancer Genetics and Cytogenetics, 1999, vol. 114 (1), pp. 22-30.
Muller K.M., et al., "New Aspects of Lung Tumor Pathology," Verhandlungen Der Deutschen Gesellschaft Fur Pathologie, 1999, vol. 83, pp. 168-183.
Supplementary European Search Report for Application No. EP10828825, mailed on Feb. 27, 2013, 12 pages.
European Patent Office Action for Application No. 10828825.9 dated Mar. 6, 2014.
United States Patent Office Action for U.S. Appl. No. 12/744,458 dated Feb. 13, 2014 (12 pages).
United States Patent Office Action for U.S. Appl. No. 12/744,458 dated Mar. 6, 2013 (12 pages).
United States Patent Office Action for U.S. Appl. No. 12/744,458 dated Sep. 23, 2014 (18 pages).
Annex to the communication and Communication from the Examining Division mailed Feb. 25, 2015 for EP Application No. EP10828825.9 filed Oct. 25, 2010.
Aviel-Ronen S., et al., "Genomic Markers for Malignant Progression in Pulmonary Adenocarcinoma with Bronchioloalveolar Features," Proceedings of the National Academy of Science, USA, 2008, vol. 105 (29), pp. 10155-10160.
Wrage M., et al., "Genomic Profiles Associated with Early Micrometastasis in Lung Cancer: Relevance of 4q Deletion," Clinical Cancer Research, 2009, vol. 15 (5), pp. 1566-1574.
Final Office Action mailed Jun. 3, 2015 for U.S. Appl. No. 12/744,458, filed Jul. 21, 2010.
European Patent Office Action for Application No. 10828825.9 dated Oct. 27, 2015.

\* cited by examiner

DETECTION OF CHROMOSOMAL ABNORMALITIES ASSOCIATED WITH PROGNOSIS OF NON SMALL CELL LUNG CANCER

CROSS REFERENCE TO A RELATED APPLICATION

This is the U.S. national stage entry of International Patent Application No. PCT/US2010/053953, filed on Oct. 25, 2010, which claims priority to U.S. provisional patent application No. 61/254,968, filed on Oct. 26, 2009 and U.S. provisional patent application No. 61/254,955, filed on Oct. 26, 2009, the contents of all of which are herein fully incorporated by reference.

FIELD OF THE INVENTION

The present disclosure relates to in vitro diagnostic assays of tissue samples from lung cancer patients for determining patient prognosis, and in particular relates to an in vitro assay for determining prognosis of early stage patients, such as those diagnosed with Stage I or Stage II non-small cell lung cancer.

BACKGROUND OF THE INVENTION

Lung cancer accounted for almost one third of cancer deaths in the United States in 2005, and is broadly classified into two types: non-small cell lung cancer and small cell lung cancer. Non-small cell lung cancer (NSCLC) comprises 80-85% of lung cancer cases in the United States. NSCLC comprises three major types: (i) Squamous cell carcinoma, which begins in squamous cells, that are thin, flat cells that look like fish scales. Squamous cell carcinoma is also called epidermoid carcinoma; (ii) Large cell carcinoma, which begins in several types of large lung cells; (iii) Adenocarcinoma, which begins in the cells that line the alveoli of the lung and make substances such as mucus. Other less common types of NSCLC include pleomorphic carcinoma, carcinoid tumor and unclassified carcinoma.

Diagnosis of NSCLC is done by a pathologist's examination of suspected tissue, such as a biopsy sample. After NSCLC diagnosis, the patient's disease is assigned a prognosis (the chance of recovery) using the patient's overall health and age, the severity of symptoms such as coughing and difficulty in breathing, the particular type of NSCLC, and the staging of the cancer. Staging takes into account the size of the tumor and whether the tumor is present in the lung only or has spread to other places in the body. The particular treatment options for a NSCLC patient are then selected based upon these considerations, and the cancer staging is an important component for treatment selection. Patients with early stage NSCLC can potentially be cured by surgical resection to remove the tumor, but the current diagnostic modalities are not able to predict which patients will recur after surgery. Cancer is a frequently fatal disease with a low cure rate, for which the majority of treatments are directed at improving the quality and duration of life. Because cancer cells are human cells, frequently distinguished only by the accumulation of a relatively small number of genetic aberrations or protein mutations, drug therapies that are useful in killing cancer cells are commonly also detrimental to many normal human cells and cause typically significant toxicities in patients who are treated. Furthermore, because cancers frequently recur locally or metastasize to tissues and organs remote from their tissue of origin, it is critical to know which patients with early stage cancers need drug treatment after surgical removal of their primary tumor. This is an especially critical issue in patients with early stage NSCLC, whose tumors were detected early and removed surgically, specifically patients with Stage I and IIa disease. Under-treating these patients with anti-cancer drugs results in an unacceptably high rate of patients developing recurrent or metastatic disease, ultimately leading to increased morbidity and death. Over-treating this population results in an unacceptably high number of patients who, not needing drug therapy, experience the toxic side effects from the drugs given to them.

The National Comprehensive Cancer Network (NCCN) internet web site describes NSCLC staging as follows. "The system most often used in United States clinical practice to describe the growth and spread of non-small cell lung cancer (NSCLC) is the TNM staging system, also known as the American Joint Committee on Cancer (AJCC) system. In TNM staging, information about the tumor (T), any spread into nearby lymph nodes (N), and any distant organ metastases (M) is combined and a stage is assigned to specific TNM groupings. The grouped stages are described using the number 0 and Roman numerals from I to IV.

"T categories are based on the lung cancer's size, its spread and location within the lungs, and its spread to nearby tissues. In the Tis category, the cancer is found only in the layer of cells lining the air passages. It has not spread into other lung tissues. This category is also known as carcinoma in situ.

"In the T1 category, the cancer is no larger than 3 centimeters (slightly less than 1¼ inches), has not spread to the visceral pleura (membranes that surround the lungs), and does not affect the main branches of the bronchi.

"In the T2 category, the cancer has one or more of the following features: (i) it is larger than 3 cm; (ii) it involves a main bronchus of a lung but is not closer than 2 cm (about 3¼ to 4 inches) to the point where the trachea (windpipe) branches into the left and right main bronchi; or (iii) has spread to the visceral pleura. The cancer may partially block the airways, but this has not caused the entire lung to collapse or develop pneumonia.

"In the T3 category, the cancer has one or more of the following features: (i) it has spread to the chest wall, the diaphragm (the breathing muscle that separates the chest from the abdomen), the mediastinal pleura (the membranes surrounding the space between the 2 lungs), or parietal pericardium (the membranes of the sac surrounding the heart); (ii) it involves a main bronchus of a lung, and it is closer than 2 cm to the point where the trachea (or windpipe) branches into the left and right main bronchi, but does not involve this area; or (iii) It has grown into the airways enough to cause one lung to entirely collapse or to cause pneumonia of the entire lung.

"In the T4 category, the cancer has one or more of the following features: (i) It has spread to the mediastinum (the space behind the chest bone and in front of the heart), the heart, the trachea (windpipe), the esophagus (the tube connecting the throat to the stomach), the backbone, or the point where the trachea branches into the left and right main bronchi; (ii) Two or more separate tumor nodules are present in the same lobe; or (iii) a malignant pleural effusion is present, which is the existence of fluid containing cancer cells in the space surrounding the lung.

"The N category depends on which, if any, of the lymph nodes near the lungs are affected by the cancer. In the N0 category, the cancer has not spread to any lymph node. In the N1 category, the cancer has spread to lymph nodes within the lung or into the hilar lymph nodes (those located around the area where the bronchus enters the lung). In N1 category the affected lymph nodes are only on the same side as the cancerous lung. In the N2 category, the cancer has spread to subcarinal lymph nodes (those which are around the point where the trachea branches into the left and right bronchi) or to lymph nodes in the mediastinum (the space behind the chest bone and in front of the heart). In the N2 category, the affected lymph nodes are on the same side of the cancerous lung. In the N3 category, the cancer has spread to lymph nodes near the collarbone on either side, and/or to the hilar or mediastinal lymph nodes on the side opposite the cancerous lung.

"The M category depends on whether the cancer has metastasized and spread to any distant tissues and organs. In the M0 category, there is no distant cancer spread. In the M1 category, the cancer has spread to 1 or more distant sites. Sites which are considered distant include other lobes of the lungs, lymph nodes further than those used to determine the N category of the cancer, and other organs or tissues such as the liver, bones, or brain.

Once the T, N, and M categories have been assigned for the particular NSCLC, this information is combined (stage grouping) to assign an overall stage of 0, I, II, III, or IV (see Table 1). Various combinations of the T and N categories are combined into stages. The stages identify tumor types that have a similar prognosis and are treated in a similar way. As noted in Table 1, a tumor with distant spread (i.e., an M1 category cancer) is considered Stage IV, regardless of tumor size of involvement of lymph nodes." The following Table from the NCCN internet web site shows the combined category and stage classification for NSCLC.

TABLE 1

| Overall Stage | T Category | N Category | M Category |
| --- | --- | --- | --- |
| Stage 0 | Tis | N0 | M0 |
| Stage IA | T1 | N0 | M0 |
| Stage IB | T2 | N0 | M0 |
| Stage IIA | T1 | N1 | M0 |
| Stage IIB | T2 | N1 | M0 |
|  | T3 | N0 | M0 |
| Stage IIIA | T1 | N2 | M0 |
|  | T2 | N2 | M0 |
|  | T3 | N1 | M0 |
|  | T3 | N2 | M0 |
| Stage IIIB | Any T | N3 | M0 |
|  | T4 | Any N | M0 |
| Stage IV | Any T | Any N | M1 |

NSCLC patients with lower stage numbers generally have a more favorable prognosis and outlook for survival, and these patients are generally treated by surgical resection of the tumor. However, even for early stage patients, such as those with Stage 1B, Stage IIA or IIB NSCLC, a significant percentage of these patients will recur after surgical resection with more aggressive disease and die. The current clinical diagnostic methods are incapable of identifying early stage NSCLC prognosis with sufficient accuracy to direct more aggressive therapy against those patients more likely to recur. Better in vitro diagnostic methods are needed to identify higher risk, early stage NSCLC patients who should receive neoadjuvant or adjuvant chemotherapy or generally have treatment opinions re-evaluated.

Molecular in vitro diagnostic assays based on fluorescence in situ hybridization (FISH) using fluorescently labeled DNA hybridization probes to identify chromosomal abnormalities have been disclosed for use in the selection of chemotherapy for NSCLC patients, (PCT/US2005/018879, "Methods for prediction of clinical outcome to epidermal growth factor inhibitors by cancer patients", M. Garcia et al.). FISH assays have been described as an initial diagnostic assay for NSCLC in U.S. Patent Application 20060063194, "Methods and probes for the detection of cancer", L. Morrison et al., published Mar. 23, 2006 (hereafter referred to as "Morrison '194"), the disclosure of which is incorporated herein by reference in its entirety. The Morrison '194 application describes multiple FISH probe sets useful for screening and diagnosis of NSCLC, and one probe set described in Morrison '194 is commercially available as the LAVysion™ probe set from Abbott Molecular, Inc. (Des Plaines, Ill., U.S.A.) under ASR (Analyte Specific Reagent) labeling for use by clinical laboratories to produce clinical diagnostic assays. Under the U.S. Food and Drug Administration ASR labeling requirements, the ASR labeling must not include any claims as to the medical utility of the ASR. The LAVysion ASR probe set comprises four FISH probes: a chromosome 5p15 locus specific probe labeled with the SpectrumGreen green fluorophore, a chromosome 8q24 locus specific probe labeled with the SpectrumGold yellow fluorophore, a chromosome 6 enumeration probe labeled with the SpectrumAqua blue fluorophore, and a chromosome 7p12 locus specific probe labeled with the SpectrumRed red fluorophore. Research performed using the LAVysion probe set has been described and is reviewed for example in K. Halling et al., "Fluorescence in situ hybridization in diagnostic cytology", Hum. Path. (2007) 38: 1137-1144.

Overexpression of cyclin E has previously been associated with poor outcome in lung cancer (reviewed in Singhal et al., Clin. Cancer Res., 2005, 11, pp. 3974-3986). However, no copy number alterations at the cyclin E locus have been established as predictive markers. Moreover, no previous reports on FISH assays for NSCLC have disclosed the use of FISH probes to more accurately identify prognosis for early stage NSCLC, in particular, those classified as Stage IB or Stage II.

SUMMARY OF THE INVENTION

In one aspect, the present disclosure provides a method of predicting disease outcome in a patient being treated for lung cancer, from a biological sample from the patient, the method comprising: contacting the sample with one or more probes for one or more chromosome regions selected from the group consisting of: 1p, 2q, 3q, 3q, 4p, 4q, 5q, 6p, 6q, 8p, 9p, 10q, 11q, 12p, 14q, 16q, 17q, and 19q; incubating the one or more probes with the sample under conditions in which each probe binds selectively with a polynucleotide sequence on its target chromosome or chromosomal region to form a stable hybridization complex; and detecting hybridization of the one or more probes, wherein a hybridization pattern showing at least one gain or loss at a chromosomal region targeted by the probes is indicative of increased risk of poor disease outcome when compared to a baseline measure of disease outcome in patients having no gain or loss at the one or more chromosomal regions targeted by the one or more probes. The patient may have a diagnosis of stage I-II non-small cell lung cancer (NSCLC). In the method, a hybridization pattern may show a gain in one or more chromosome regions selected from the group consisting of 1p, 2q, 6p, 6q, 8p, 11q, 12p, 17q, and 19q, or the group consisting of 1p, 6p, 6q, 11q, 12p and 19q, which is indicative of poor disease outcome in the patient. A hybridization pattern may show a loss in one or more chromosome regions selected from the group consisting of: 2q, 3q, 4p, 4q, 5q, 9p, 10q, 14q and 16q, or the group consisting of 4q, 5q, 9p, and 16q, which is indicative of poor disease outcome in the patient.

In the methods, the one or more probes can be for one or more chromosome subregions selected from the group consisting of: 1q13, 2q22-q23, 2q24, 2q33, 2q34, 3q11, 3q13, 4p13, 4p12, 4q21, 4q24, 5q11, 5q12, 5q13, 5q15, 6p21, 6q13, 6q22-q23, 8p23, 9p35, 9p13, 10q11-q21, 11q12-q13, 11q13, 12p13, 14q12, 14q21, 14q22-q23, 14q23-24, 16q12, 17q21, 17q22, 17q25, 19q12, and 19q13, including in particular 1q13.3, 2q22.3-q23.3, 2q24.2, 2q33.3, 2q34, 3q11.2, 3q13.3, 4p13, 4p12, 4q21.21-q22, 4q24, 5q11.2, 5q12.1, 5q13.1-q13.2, 5q15, 6p21.2, 6q21.3, 6q13, 6q22.3-q23.3, 8p23.1, 9p35.3, 9p13.2, 10q11.23-q21.1, 11q12.2-q13.1, 11q13.1, 12p13.3, 14q12, 14q21.1, 14q21.3, 14q22.1, 14q22.1-23.1, 14q22.3-q23.1, 14q23.2-q24.1, 16q12.1, 17q21.32-q21.33, 17q22, 17q25.1, 19q12, 19q13.11-q13.12 and 19q13.33-q13.43.

In the methods, the sample may be contacted with a combination of at least two, at least three, or at least four probes, each probe targeting a different chromosome subregion, wherein each of the probes are for a chromosomal subregion selected from the group consisting of: 1q13, 2q22-q23, 2q24, 2q33, 2q34, 3q11, 3q13, 4p13, 4p12, 4q21, 4q24, 5q11, 5q12, 5q13, 5q15, 6p21, 6q13, 6q22-q23, 8p23, 9p35, 9p13, 10q11-q21, 11q12-q13, 11q13, 12p13, 14q12, 14q21, 14q22-q23, 14q23-24, 16q12, 17q21, 17q22, 17q25, 19q12, and 19q13, wherein a hybridization pattern showing a gain or loss in one or more of the chromosome subregions is indicative of poor disease outcome in the patient. The sample may be contacted for example with a combination of at least two probes for a set of chromosome subregions including 19q12 and 19q13, or for a set of chromosome subregions including 11q12 and 11q13.

In any of the methods, the probe combination may distinguish samples comprising stage I-II NSCLC at increased risk of poor disease outcome from samples that do not comprise stage I-II NSCLC at increased risk of poor disease outcome, with a sensitivity of at least 93% and a specificity of at least 90%. The sensitivity may be at least 95% and the specificity at least 90.4%, or the sensitivity may be at least 96% and the specificity at least 91%.

In any of the methods, the probe combination may comprise, for example, ten probes or fewer, or eight probes or fewer. Thus the probe combination may comprise 10, 9, 8, 7, 6, 5, 4, 3, or 2 probes, or 1 probe.

In any of the methods, the method may be carried out by array comparative genomic hybridization (aCGH) to probes immobilized on a substrate. Further, in any of the methods the method may be carried out by fluorescence in situ hybridization (FISH), wherein each probe in the probe combination is labeled with a different fluorophore.

In any of the methods, the biological sample may be for example a lung biopsy specimen.

In another aspect, the present disclosure provides a combination of probes comprising 2, 3, 4, 5, 6, 7, 8, 9 or 10 probes selected from any of the groups of probes as set forth herein above. A probe combination may have a sensitivity of at least 93% and a specificity of at least 90% for distinguishing samples comprising stage I-II NSCLC at increased risk of poor disease outcome from samples that do not comprise stage I-II NSCLC at poor disease outcome. The sensitivity may be at least 95% and the specificity at least 90.4%, or the sensitivity at least 96% and the specificity at least 91%. The probe combination may contain, for example, 10 or fewer probes, or 8 or fewer probes, and thus for example may contain 10, 9, 8, 7, 6, 5, 4, 3, or 2 probes, or 1 probe.

In another aspect, the present disclosure provides a kit for predicting disease outcome in a patient being treated for lung cancer, from a biological sample from the patient, wherein the kit comprises a combination of probes comprising between 2 and 10 probes selected from any of the groups of probes as set forth herein above. In the kit, the combination of probes may have a sensitivity of at least 93% and a specificity of at least 90% for distinguishing samples comprising stage I-II NSCLC at increased risk of poor disease outcome from samples that do not comprise stage I-II NSCLC at poor disease outcome, or the sensitivity may be at least 95% and the specificity at least 90.4%, or the sensitivity may be is least 96% and the specificity at least 91%. In the kit, the probe combination may comprise 10 or fewer probes, or 8 or fewer probes, and thus for example may contain 10, 9, 8, 7, 6, 5, 4, 3, or 2 probes, or 1 probe.

DETAILED DESCRIPTION

Figure 1:
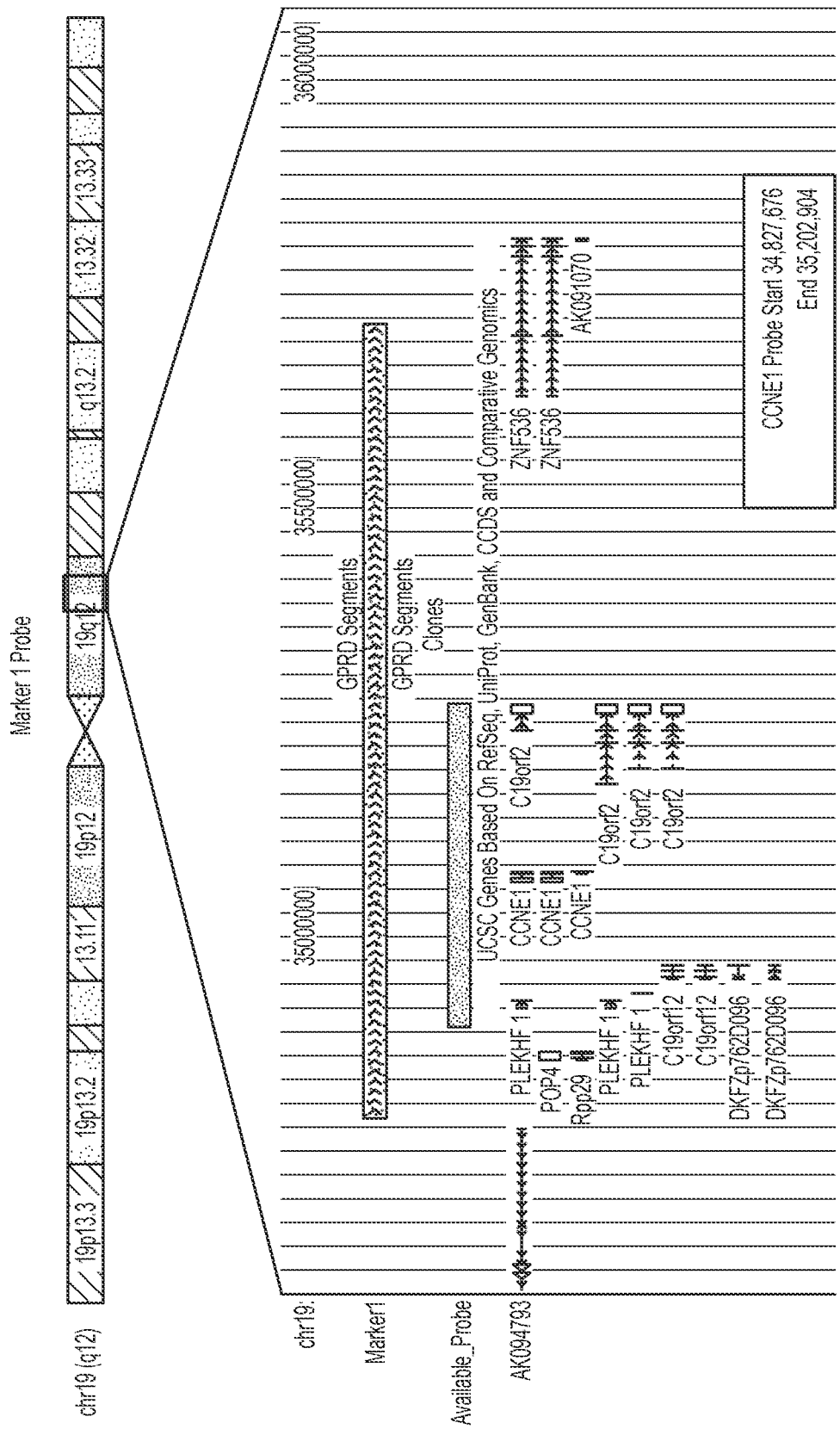
FIG. 1 is a chromosomal map of a probe to "marker 1" on Chr19, at 19q12.

Previously described expression-based markers of poor disease outcome in cancer cannot be measured with FISH, a well-established clinical diagnostic tool. Until now, no gene amplifications/deletions have been identified that can predict disease outcome. The inventors have discovered changes, i.e., amplifications and deletions, in certain chromosomal sequences in certain cancer patients. Moreover, the inventors have determined that these changes are statistically significantly associated with shorter overall survival or reduced time to recurrence in stage I-II NSCLC. The present disclosure thus provides a method of detection of chromosomal abnormalities associated with prognosis of NSCLC, as well as probe combinations and diagnostic kits. The methods can utilize techniques known as Comparative Genomic Hybridization on a microarray (aCGH) and Fluorescence In Situ Hybridization (FISH) assay using a combination of Locus Specific Identifier (LSI) and Chromosome Enumerator (CEP) probes to detect cells that have chromosomal abnormalities consistent with certain disease outcomes in stage I-II NSCLC. Accordingly, the present disclosure provides methods of determining prognosis of early stage non-small cell lung cancer (NSCLC) in a human by assessment of the copy number of chromosomal DNA at any one of forty-seven markers.

Advantages of the methods described herein can include one or more of the following: use of stable DNA for detection of chromosomal abnormalities (deletion, amplification, aneusomy, translocation); rapid detection: results could be obtained in 18-36 hours; implementation possibilities include multiplexed methods (e.g., microarray) and multicolor FISH; use as stand-alone test or as adjuncts to other tests (histology, PSA, nomogram, methylation, mutation); use on cytology specimens or biopsy (fresh-frozen or FFPE); combination of several probes increases sensitivity and specificity as compared to a single-analyte assay; increased sensitivity compared to conventional cytology.

1. Definitions

Terms used in the claims and specification are defined as set forth below unless otherwise specified.

The terms "non-small cell lung cancer" and "NSCLC" as used interchangeably herein refer to a malignant neoplasm of the lung which is not of the oat cell (or small cell) type, and includes but is not limited to the recognized types of bronchogenic carcinomas (those arising from the lining of the bronchi) including adenocarcinoma, squamous cell carcinoma, and large cell undifferentiated carcinoma. Different stages of NSCLC are recognized based on growth and spread of the cancer according to the TNM staging system, or American Joint Committee on Cancer (AJCC) system as set forth for example herein above in Table 1, and include the early stages IA, IB, IIA and IIB, sometimes referred to collectively herein as stage I-II.

The terms "tumor" or "cancer" in an animal refer to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. The term tumor includes both benign and malignant neoplasms. The term "neoplastic" refers to both benign and malignant atypical growth.

The term "biological sample" or "specimen" refers to an amount of bodily tissue or cells obtained from a subject suspected of having, or having NSCLC. In some embodiments, the sample includes a formalin-fixed paraffin-embedded biopsy. In addition to subjects having or suspected of having NSCLC, the biological sample may further be derived from a subject having a diagnosis of early stage (stage I-II) NSCLC. The biological sample or specimen may be derived from a lung biopsy specimen which may be obtained for example by any known method such as needle biopsy, bronchoscopic biopsy, open biopsy or video-assisted thorascopic surgery.

The terms "nucleic acid" or "polunucleotide," as used herein, refer to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36: 8692-8698), and benzylphosphonate linkages (Samstag (1996) Antisense Nucleic Acid Drug Dev 6: 153-156).

The terms "hybridizing specifically to," "specific hybridization," and "selectively hybridize to," as used herein, refer to the binding, duplexing, or hybridizing of a nucleic acid molecule preferentially to a particular nucleotide sequence under stringent conditions. The term "stringent conditions" refers to conditions under which a probe will hybridize preferentially to its target sequence, and to a lesser extent to, or not at all to, other sequences. A "stringent hybridization" and "stringent hybridization wash conditions" in the context of nucleic acid hybridization (e.g., as in array, Southern or Northern hybridization, or FISH) are sequence-dependent, and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) Molecular Cloning: A Laboratory Manual (3rd ed.) Vol. 1-3, Cold Spring Harbor Laboratory, Cold Spring Harbor Press, NY, and detailed discussion, below).

A "chromosomal probe" or "chromosomal probe composition" refers to one or more polynucleotides that specifically hybridize to a region of a chromosome. The target sequences to which the probe can bind vary in length, e.g., from about 25,000 nucleotides to about 800,000 nucleotides. Smaller probes, e.g., that hybridize to a region of less than 100,000 nucleotides, or to a region of less than 10,000 nucleotides, can also be employed. Thus, in various embodiments, the probe can hybridize target sequences that are 25,000 nucleotides, 30,000 nucleotides, 50,000 nucleotides, 100,000 nucleotides, 150,000 nucleotides, 200,000 nucleotides, 250,000 nucleotides, 300,000 nucleotides, 350,000 nucleotides, 400,000 nucleotides, 450,000 nucleotides, 500,000 nucleotides, 550,000 nucleotides, 600,000 nucleotides, 650,000 nucleotides, 700,000 nucleotides, 750,000 nucleotides, or 800,00 nucleotides in length or that have a length falling in any range having any of these values as endpoints. A probe to a particular chromosomal region can include multiple polynucleotide fragments, e.g., ranging in size from about 50 to about 1,000 nucleotides in length.

A chromosome enumeration probe (CEP) is any probe able to enumerate the number of specific chromosomes in a cell.

The term "label containing moiety" or "detection moiety" generally refers to a molecular group or groups associated with a chromosomal probe, either directly or indirectly, that allows for detection of that probe upon hybridization to its target.

The term "target region" or "nucleic acid target" refers to a nucleotide sequence that resides at a specific chromosomal location whose loss and/or gain is indicative of the presence of NSCLC.

2. Introduction

The methods described herein are based, in part, on the identification of highly sensitive and specific chromosomal probes and probe combinations that can be used to selectively detect stage I-II NSCLC at increased risk of poor disease outcome. The probe combinations of two or more probes provide higher sensitivity and specificity than individual probes. The probes encompass locus-specific probes as well as chromosome enumeration probes (CEPs), which typically hybridize to centromeric regions. The methods are carried by hybridizing one or more probes to nucleic acids from, e.g., cytology specimens (lung biopsy specimens) or cells from frozen specimens or fixed specimens, such as formalin-fixed, paraffin-embedded tissue.

The present disclosure includes methods for determining prognosis of NSCLC patients classified as early-stage cancers, in particular those classified as Stage IA, Stage IB, Stage IIA or Stage IIB (Stage IIA and IIB are collectively referred to as Stage II) using the widely used TNM staging system. Alternate NSCLC staging systems based upon other diagnostic classifications can be used to identify the patients whose tissue sample may be assayed by the methods disclosed herein. As used herein, "early stage NSCLC" refers to a NSCLC tumor that has not spread to more than one lymph node, nor metastasized to any other organ. Early-stage NSCLC patients are almost always treated by surgical resection seeking complete tumor removal, yet a significant risk of recurrence exists for these early stage patients even where the tumor is believed to be completely resected. Current diagnostic modalities do not permit accurate prediction of which of these early stage cancers are high risk for recurrence and thus should be treated post-resection with adjuvant chemotherapy or before the resection using neo-adjuvant chemotherapy. The present disclosure provides prognostic identification of those early stage patients at higher risk by determining the gene copy number in the patient sample.

Thus in one aspect, the methods encompass a method of predicting disease outcome in a patient being treated for lung cancer. A test sample, which is a biological sample from the patient, is provided, and a copy number for a selected cancer outcome marker in the test sample is determined. The copy number from the test sample is compared against a baseline copy number of two, thereby determining the presence or absence of a copy number change for the cancer outcome marker. Based on the presence or absence of a copy number change for the cancer outcome marker in the test sample, the patient is identified as having an increased risk of a poor disease outcome when compared to a baseline measure of disease outcome in patients having no copy number change for the cancer outcome marker. The presence of a copy number change for the cancer outcome marker, i.e., a copy number of greater than 2 due to amplification, or less than 2 due to deletion, is predictive of poor disease outcome. The poor disease outcome is at least one of a decreased overall survival time when compared to an overall survival time of patients having no copy number change in the cancer outcome marker, and a shorter time to recurrence when compared to the time to recurrence for patients having no copy number change in the cancer outcome marker. The methods also encompass a method of predicting disease outcome in a patient being treated for lung cancer, in which based on the presence or absence of a copy number change in the cancer outcome marker, a determination is made as to whether the patient has a higher risk of a decreased overall survival time or a shorter time to recurrence when compared to an overall survival time of patients having no copy number change in the cancer outcome marker.

3. Chromosomal Probes

Probes for use in the invention are used for hybridization to nucleic acids that are present in biological samples from subjects having a diagnosis of stage I-II NSCLC or suspected of having NSCLC which may be at any stage. In certain embodiments, the probes are labeled with detectable labels, e.g., fluorescent labels.

a. Chromosome Enumeration Probe

A chromosome enumeration probe typically recognizes and binds to a region near to (referred to as "peri-centromeric") or at the centromere of a specific chromosome, typically a repetitive DNA sequence. The centromere of a chromosome is typically considered to represent that chromosome entity since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals for the corresponding centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome.

In lieu of a centromeric probe for a chromosome, one of skill in the art will recognize that a chromosomal arm probe may alternately be used to approximate whole chromosomal loss or gain. However, such probes are not as accurate at enumerating chromosomes since the loss of signals for such probes may not always indicate a loss of the entire chromosomes. Examples of chromosome enumeration probes include CEP® probes (e.g., CEP® 12 and X/Y probes) commercially available from Abbott Molecular, DesPlaines, Ill. (formerly Vysis, Inc., Downers Grove, Ill.).

Chromosome enumerator probes and locus-specific probes that target a chromosome region or subregion can readily be prepared by those in the art or can be obtained commercially, e.g., from Abbott Molecular, Molecular Probes, Inc. (Eugene, Oreg.), or Cytocell (Oxfordshire, UK). Such probes are prepared using standard techniques. Chromosomal probes may be prepared, for example, from protein nucleic acids, cloned human DNA such as plasmids, bacterial artificial chromosomes (BACs), and P1 artificial chromosomes (PACs) that contain inserts of human DNA sequences. A region of interest may be obtained via PCR amplification or cloning. Alternatively, chromosomal probes may be prepared synthetically.

b. Locus-Specific Probes

Probes that can be used in the method described herein include probes that selectively hybridize to chromosome regions, e.g., 1p, 2q, 3q, 3q, 4p, 4q, 5q, 6p, 6q, 8p, 9p, 10q, 11q, 12p, 14q, 16q, 17q, and 19q; or subregions of the chromosome regions, e.g., 1q13, 2q22-q23, 2q24, 2q33, 2q34, 3q11, 3q13, 4p13, 4p12, 4q21, 4q24, 5q11, 5q12, 5q13, 5q15, 6p21, 6q13, 6g22-q23, 8p23, 9p35, 9p13, 10q11-q21, 11q12-q13, 11q13, 12p13, 14q12, 14q21, 14q22-q23, 14g23-24, 16q12, 17q21, 17q22, 17q25, 19q12, and 19q13; or 1q13.3, 2q22.3-q23.3, 2q24.2, 2q33.3, 2q34, 3q11.2, 3q13.3, 4p13, 4p12, 4q21.21-q22, 4q24, 5q11.2, 5q12.1, 5q13.1-q13.2, 5q15, 6p21.2, 6q21.3, 6q13, 6q22.3-q23.3, 8p23.1, 9p35.3, 9p13.2, 10q11.23-q21.1, 11q12.2-q13.1, 11q13.1, 12p13.3, 14q12, 14q21.1, 14q21.3, 14q22.1, 14q22.1-23.1, 14q22.3-q23.1, 14g23.2-q24.1, 16q12.1, 17q21.32-q21.33, 17q22, 17q25.1, 19q12, 19q13.11-q13.12 and 19g13.33-g13.43. (The subregion designations as used herein include the designated band and typically about 10 megabases of genomic sequence to either side.) Such probes are also referred to as "locus-specific probes." A locus-specific probe selectively binds to a specific locus at a chromosomal region that is known to undergo gain or loss in NSCLC, particularly stage I-II NSCLC, and particularly those stage I-II NSCLC patients at increased risk of poor disease outcome. A probe can target coding or non-coding regions, or both, including exons, introns, and/or regulatory sequences, such as promoter sequences and the like.

When targeting of a particular gene locus is desired, probes that hybridize along the entire length of the targeted gene are preferred in some embodiments, although not required. In specific embodiments, a locus-specific probe can be designed to hybridize to an oncogene or tumor suppressor gene, the genetic aberration of which is correlated with an increased risk of poor disease outcome in NSCLC.

Probes useful in the methods described herein generally include a collection of one or more nucleic acid fragments whose hybridization to a target can be detected. Probes can be produced from a source of nucleic acids from one or more particular (preselected) portions of the genome, for example one or more clones, an isolated whole chromosome or chromosome fragment, or a collection of polymerase chain reaction (PCR) amplification products. Probes useful in the method described herein can be produced from nucleic acids found in the regions described herein. The probe may be processed in some manner, for example, by blocking or removal of repetitive nucleic acids or enrichment with unique nucleic acids.

In certain aspects, e.g., in FISH-based methods, locus-specific probe targets preferably include at least 100,000 nucleotides. For cells of a given sample, relative to those of a control, increases or decreases in the number of signals for a probe indicate a gain or loss, respectively, for the corresponding region. Probes may also be employed as isolated nucleic acids immobilized on a solid surface (e.g., nitrocellulose), as in aCGH. In some embodiments, the probes may be members of an array of nucleic acids as described, for instance, in WO 96/17958, which is hereby incorporated by reference it its entirety and specifically for its description of array CGH. Techniques capable of producing high density arrays are well-known (see, e.g., Fodor et al. Science 767-773 (1991) and U.S. Pat. No. 5,143,854), both of which are hereby incorporated by reference for this description.

As described in detail below, loci that were putatively associated with increased risk of poor disease outcome in NSCLS were identified. These include regions of chromosomal DNA, the amplification of which produces a copy number gain at the particular locus, wherein the copy number gain is associated with a poor disease outcome. These cancer outcome markers include Chr 19, 34.7 Mb-35.6 Mb; Chr 19, 38.9-40.7 Mb; Chr 17, 69.2-71.3 Mb; Chr 6, 70.8-71.1 Mb; Chr 12, 93.7 kb-1.9Mb; Chr 11, 64.3-64.8 Mb; Chr 19, 57.0-62.2 Mb; Chr 6, 39.1-39.9 Mb; Chr 11, 64.8-65.7 Mb; Chr 11, 61.4-64.3 Mb; Chr 17, 51.5-53.2 Mb; Chr 17, 43.5-44.9 Mb; Chr 2, 147.6-151.1 Mb; Chr 6, 123.7-135.6 Mb; Chr 8, 6.9-8.8 Mb; Chr 2, 159.9-161.4 Mb; Chr 2, 200.9-204.2 Mb; Chr 6, 36.3-36.7 Mb; Chr 2, 205.9-208.1 Mb; and Chr 1, 109.5-111.1 Mb. These loci also include regions of chromosomal DNA, the deletion of which produces a copy number loss at the locus, wherein the copy number loss is associated with a poor disease outcome. These cancer outcome markers (deletion markers or "DelMarkers") include Chr 5, 62.9-67.8 Mb; Chr 5, 53.3-53.8 Mb; Chr 4, 105.8-107.2 Mb; Chr 16, 45.8-46.3 Mb; Chr 5, 50.7-52.0 Mb; Chr 5, 94.2-96.1 Mb; Chr 9, 36.1-37.0 Mb; Chr 5, 94.2-96.1 Mb; Chr14, 51.1-52.8 Mb; Chr 14, 61.5-68.6 Mb; Chr 9, 28.1 Mb; Chr 4, 43.7-44.2 Mb; Chr 5, 60.8-62.9 Mb; Chr 3, 120.0-121.1 Mb; Chr 4, 46.2-48.0 Mb; Chr 14, 38.9-40.0 Mb; Chr 4, 44.2-44.6 Mb; Chr 2, 213.7-214.3 Mb; Chr14, 43.9-46.6 Mb; Chr 14, 27.6-28.6 Mb; Chr 3, 98.0-98.3 Mb; Chr14, 55.2-60.0 Mb; Chr14, 48.7-51.1 Mb; Chr 4, 81.4-83.2 Mb; Chr 10, 51.9-54.2 Mb; Chr 5, 55.2-58.6 Mb; and Chr 5, 67.8-68.5 Mb.

New FISH probes were developed for these markers, which are listed in Table 10 in the Examples herein below, together with their corresponding chromosomal start and end positions, and start and end bands. Chromosomal regions targeted by the probes include 1p, 2q, 3q, 3q, 4p, 4q, 5q, 6p, 6q, 8p, 9p, 10q, 11q, 12p, 14q, 16q, 17q, and 19q. Those chromosomal regions in which a gain is indicative of poor disease outcome in the patient include 1p, 2q, 6p, 6q, 8p, 11q, 12p, 17q, and preferably 19q, 1p, 6p, 6q, 11q, 12p and 19q. Those chromosomal regions in which a loss is indicative of poor disease outcome in the patient include 2q, 3q, 4p, 4q, 5q, 9p, 10q, 14q and 16q, and preferably 4q, 5q, 9p, and 16q. Chromosomal subregions targeted by the probes include 1q13, 2q22-q23, 2q24, 2q33, 2q34, 3q11, 3q13, 4p13, 4p12, 4q21, 4q24, 5q11, 5q12, 5q13, 5q15, 6p21, 6q13, 6q22-q23, 8p23, 9p35, 9p13, $10_g11$-q21, 11q12-q13, 11q13, 12p13, 14q12, 14q21, 14q22-q23, 14q23-24, 16q12, 17q21, 17q22, 17q25, 19q12, and 19q13, and more particularly 1q13.3, 2q22.3-q23.3, 2q24.2, 2q33.3, 2q34, 3q11.2, 3q13.3, 4p13, 4p12, 4q21.21-q22, 4q24, 5q11.2, 5q12.1, 5q13.1-q13.2, 5q15, 6p21.2, 6q21.3, 6q13, 6q22.3-q23.3, 8p23.1, 9p35.3, 9p13.2, $10_g11.23$-q21.1, 11q12.2-q13.1, 11q13.1, 12p13.3, 14q12, 14q21.1, 14q21.3, 14q22.1, 14q22.1-23.1, 14q22.3-q23.1, 14q23.2-q24.1, 16q12.1, 17q21.32-q21.33, 17q22, 17q25.1, 19q12, 19q13.11-q13.12 and 19q13.33-q13.43.

c. Probe Selection Methods

Probe combinations can be selected for their ability to identify whether the patient is at increased risk of a poor disease outcome following a diagnosis of early stage NSCLC. Alternatively, probe combinations can be selected for their ability to guide selection of a treatment for a patient suffering from lung cancer. For example, when treatment with a chemotherapy agent is at least one treatment option for the patient, probe combinations can be used to help determine a chemotherapy treatment regimen, including selection of a chemotherapy agent and determining a frequency of chemotherapy treatment. For example, the choice of a particular chemotherapy agent and schedule of treatment may be guided by the knowledge that the patient is not at increased risk of having a poor disease outcome, or conversely that the patient is at increased risk of a poor disease outcome. Alternatively, probe combinations can be used to classify a patient as having a lung cancer that is resistant to standard treatment, based on the presence of a copy number change in two or more cancer outcome markers.

Probe combinations for use in the methods of the present disclosure can be selected using principles well known to the routineer and as described in the examples. Combinations of chromosomal probes within a probe combination are chosen for sensitivity, specificity, and detectability regarding increased risk of poor disease outcome in NSCLC. Sensitivity refers to the ability of a test (e.g., FISH) to detect increased risk of poor disease outcome for a patient with NSCLC (shorter survival time or shorter time to recurrence) when the increased risk is present. More precisely, sensitivity is defined as True Positives/(True Positives +False Negatives). A test with high sensitivity has few false negative results, while a test with low sensitivity has many false negative results. In particular embodiments, the combination of probes has a sensitivity of least about: 93, 94, 95, 96, 97, 98, 99, or 100%, or a sensitivity falling in a range with any of these values as endpoints.

Specificity, on the other hand, refers to the ability of test (e.g. FISH) to give a negative result when disease is not present. More precisely, specificity is defined as True Negatives/(True Negatives+False Positives). A test with high specificity has few false positive results, while a test with a low specificity has many false positive results. In certain embodiments, the combination of probes has a specificity of at about: 88, 89, 90, 91, 92, 93, 94, or 95%, or a specificity falling in a range with any of these values as endpoints.

In general, chromosomal probe combinations with the highest combined sensitivity and specificity for the detection of higher risk of poor disease outcome in NSCLC are preferred. In exemplary embodiments the combination of probes has a sensitivity and specificity of at least about: 93% and 88%, 95% and 90%, 96% and 91%, 97% and 92%, respectively, or any combination of sensitivity and specificity based on the values given above for each of these parameters.

The combined sensitivity and specificity of a probe combination can be represented by the parameter distance from ideal (DFI), defined as $[(1-sensitivity)^2+(1-specificity)^2]^{1/2}$ DFI values range from 0 to 1.414, with 0 representing a probe combination having 100% sensitivity and 100% specificity and 1.414 representing a probe combination with 0% sensitivity and 0% specificity.

There is no limit to the number of probes that can be employed in a combination. For example, 5 probes can be combined, 10 probes can be combined, 20 probes can be combined, 30 probes can be combined, 40 probes can be combined, 50 probes can be combined, etc. Although, in certain embodiments, no more than ten (10) probes are combined. Additionally, in some embodiments, the number of probes within a set that is to be viewed by a human observer (and not with computer assisted imaging techniques) may be restricted for practical reasons, e.g., by the number of unique fluorophores that provide visually distinguishable signals upon hybridization. For example, typically four or five unique fluorophores (e.g., which appear as red, green, aqua, and gold signals to the human eye) can be conveniently employed in a single probe combination. Generally, the sensitivity of an assay increases as the number of probes in a set increases. However, the increases in sensitivity become smaller and smaller with the addition of more probes and at some point the inclusion of additional probes to a probe combination is not associated with significant increases in the sensitivity of the assay ("diminishing returns"). Increasing the number of probes in a probe combination may decrease the specificity of the assay. Accordingly, a probe combination of the present disclosure typically includes two, three, or four chromosomal probes, as necessary to provide optimal balance between sensitivity and specificity.

Individual probes can be chosen for inclusion in a probe combination based on their ability to complement other probes within the combination. Specifically, they are targeted to chromosomes or chromosomal subregions that are not frequently altered simultaneously within a given NSCLC patient. Thus, each probe in a probe combination complements the other(s), i.e., identifies increased risk of poor disease outcome in NSCLC where the other probes in the combination sometime fail to identify. One method for determining which probes complement one another is to identify single probes with the lowest DFI values for a group of tumor specimens. Then additional probes can be tested on the tumor samples that the initial probe failed to identify, and the probe with the lowest DFI value measured in combination with the initial probe(s) is added to the set. This may then be repeated until a full set of chromosomal probes with the desired DFI value is achieved.

Discrimination analysis is one method that can be used to determine which probes are best able to detect higher risk of poor disease outcome in NSCLC. This method assesses if individual probes are able to detect a statistically different percentage of abnormal cells in test specimens (e.g., lung biopsies) when compared to normal specimens. The detection of cells with chromosomal (or locus) gains or chromosomal (or locus) losses can both be used to identify patients at higher risk of poor disease outcome in NSCLC. However, chromosomal losses sometimes occur as an artifact in normal cells because of random signal overlap and/or poor hybridization. In sections of formalin-fixed paraffin-embedded material, commonly used to assess biopsies, truncation of nuclei in the sectioning process can also produce artifactual loss of chromosomal material. Consequently, chromosomal gains are often a more reliable indicator of the presence of neoplastic cells.

Cutoff values for individual chromosomal gains and losses must be determined when choosing a probe combination. The term "cutoff value" is intended to mean the value of a parameter associated with chromosomal aberration that divides a population of specimens into two groups—those specimens above the cutoff value and those specimens below the cutoff value. For example, the parameter may be the absolute number or percentage of cells in a population that have genetic aberrations (e.g., losses or gains for target regions). If the number or percentage of cells in the specimen harboring losses or gains for a particular probe is higher than the cutoff value, the sample is determined to be positive for increased risk of poor disease outcome in NSCLC.

Useful probe combinations are discussed in Example 3 below. In exemplary combinations, a copy number gain at two or more chromosome subregions including 19q12 and 19q13, and/or two or more chromosome subregions including 11q12 and 11q13, are indicative of increased risk of poor disease outcome in NSCLC. Thus, useful probe combinations include at a combination of at least two probes for a set of chromosome subregions including 19q12 and 19q13, or a combination of at least two probes for a set of chromosome subregions including 11q12 and 11q13.

4. Probe Hybridization

Conditions for specifically hybridizing the probes to their nucleic acid targets generally include the combinations of conditions that are employable in a given hybridization procedure to produce specific hybrids, the conditions of which may easily be determined by one of skill in the art. Such conditions typically involve controlled temperature, liquid phase, and contact between a chromosomal probe and a target. Hybridization conditions vary depending upon many factors including probe concentration, target length, target and probe G-C content, solvent composition, temperature, and duration of incubation. At least one denaturation step may precede contact of the probes with the targets. Alternatively, both the probe and nucleic acid target may be subjected to denaturing conditions together while in contact with one another, or with subsequent contact of the probe with the biological sample. Hybridization may be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, use of a blocking agent such as unlabeled blocking nucleic acid as described in U.S. Pat. No. 5,756,696 (the contents of which are herein incorporated by reference in their entirety, and specifically for the description of the use of blocking nucleic acid), may be used in conjunction with the methods of the present disclosure. Other conditions may be readily employed for specifically hybridizing the probes to their nucleic acid targets present in the sample, as would be readily apparent to one of skill in the art.

Upon completion of a suitable incubation period, non-specific binding of chromosomal probes to sample DNA may be removed by a series of washes. Temperature and salt concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes may be carried out at a temperature in the range of about 65 to about 80° C. with about 0.2× to about 2×SSC and about 0.1% to about 1% of a non-ionic detergent such as Nonidet P-40 (NP40). If lower stringency washes are required, the washes may be carried out at a lower temperature with an increased concentration of salt.

5. Detection of Probe Hybridization Patterns

The hybridization probes can be detected using any means known in the art. Label-containing moieties can be associated directly or indirectly with chromosomal probes. Different label-containing moieties can be selected for each individual probe within a particular combination so that each hybridized probe is visually distinct from the others upon detection. Where FISH is employed, the chromosomal probes can conveniently be labeled with distinct fluorescent label-containing moieties. In such embodiments, fluorophores, organic molecules that fluoresce upon irradiation at a particular wavelength, are typically directly attached to the chromosomal probes. A large number of fluorophores are commercially available in reactive forms suitable for DNA labeling.

Attachment of fluorophores to nucleic acid probes is well known in the art and may be accomplished by any available means. Fluorophores can be covalently attached to a particular nucleotide, for example, and the labeled nucleotide incorporated into the probe using standard techniques such as nick translation, random priming, PCR labeling, and the like. Alternatively, the fluorophore can be covalently attached via a linker to the deoxycytidine nucleotides of the probe that have been transaminated. Methods for labeling probes are described in U.S. Pat. No. 5,491,224 and Molecular Cytogenetics: Protocols and Applications (2002), Y.-S. Fan, Ed., Chapter 2, "Labeling Fluorescence In Situ Hybridization Probes for Genomic Targets," L. Morrison et al., p. 21-40, Humana Press, both of which are herein incorporated by reference for their descriptions of labeling probes.

Exemplary fluorophores that can be used for labeling probes include TEXAS RED (Molecular Probes, Inc., Eugene, Oreg.), CASCADE blue aectylazide (Molecular Probes, Inc., Eugene, Oreg.), SPECTRUMORANGE™ (Abbott Molecular, Des Plaines, Ill.) and SPECTRUMGOLD™ (Abbott Molecular).

One of skill in the art will recognize that other agents or dyes can be used in lieu of fluorophores as label-containing moieties. Luminescent agents include, for example, radioluminescent, chemiluminescent, bioluminescent, and phosphorescent label containing moieties. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes may be achieved as described above for FISH.

Chromosomal probes hybridized to target regions may alternatively be visualized by enzymatic reactions of label moieties with suitable substrates for the production of insoluble color products. Each probe may be discriminated from other probes within the set by choice of a distinct label moiety. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzidine serves as a substrate for In embodiments where fluorophore-labeled probes or probe compositions are used, the detection method can involve fluorescence microscopy, flow cytometry, or other means for determining probe hybridization. Any suitable microscopic imaging method may be used in conjunction with the methods of the present disclosure for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems, BioView or Applied Imaging systems may alternatively be used.

In array CGH, the probes are not labeled, but rather are immobilized at distinct locations on a substrate, as described in WO 96/17958. In this context, the probes are often referred to as the "target nucleic acids." The sample nucleic acids are typically labeled to allow detection of hybridization complexes. The sample nucleic acids used in the hybridization may be detectably labeled prior to the hybridization reaction. Alternatively, a detectable label may be selected which binds to the hybridization product. In dual- or mult-color aCGH, the target nucleic acid array is hybridized to two or more collections of differently labeled nucleic acids, either simultaneously or serially. For example, sample nucleic acids (e.g., from lung biopsy) and reference nucleic acids (e.g., from normal lung) are each labeled with a separate and distinguishable label. Differences in intensity of each signal at each target nucleic acid spot can be detected as an indication of a copy number difference. Although any suitable detectable label can be employed for aCGH, fluorescent labels are typically the most convenient.

Preferred methods of visualizing signals are described in WO 93/18186, which is hereby incorporated by reference for this description. To facilitate the display of results and to improve the sensitivity of detecting small differences in fluorescence intensity, a digital image analysis system can be used. An exemplary system is QUIPS (an acronym for quantitative image processing system), which is an automated image analysis system based on a standard fluorescence microscope equipped with an automated stage, focus control and filterwheel (Ludl Electronic Products, Ltd., Hawthorne, N.Y.). The filterwheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display which is used for finding interesting areas on a slide as well as for focusing. The other camera port has a cooled CCD camera (model 200 by Photometrics Ltd., Tucson, Ariz.) which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

6. Screening and Diagnosis of Patients for NSCLC

The detection methods of the invention include obtaining a biological sample from a subject having NSCLC or suspected of having NSCLC. The biological sample can be a cytology specimen. The biological sample may be a frozen or fixed specimen, such as formalin-fixed and paraffin embedded specimen. Typically for a lung cancer patient the biological sample is a tissue sample such as a peripheral blood sample that contains circulating tumor cells, or a lung tumor tissue biopsy or resection (e.g., lung biopsy obtained by needle biopsy, bronchoscopic biopsy, open biopsy or video-assisted thorascopic biopsy). Other suitable tissue samples include for example a thin layer cytological sample, a fine needle aspirate sample, a lung wash sample, a pleural effusion sample, a fresh frozen tissue sample, a paraffin embedded tissue sample or an extract or processed sample produced from any of a peripheral blood sample. Preferably, the sample has been classified as an early stage cancer, for example, such as any of Stage IA, Stage IB, Stage IIA or Stage IIB, according to generally accepted staging practice, for example using pathological stages.

The sample is contacted with one or more chromosomal probe(s) to selectively detect increased risk of poor disease outcome in NSCLC in the sample, if any, under conditions for specifically hybridizing the probes to their nucleic acid targets present in the sample. Probes of a combination can be hybridized concurrently or sequentially with the results of each hybridization imaged digitally, the probe or probes stripped, and the sample thereafter hybridized with the remaining probe or probes. Multiple probe combinations can also be hybridized to the sample in this manner.

As noted, a biological sample can be treated with a fixative such as formaldehyde and embedded in paraffin and sectioned for use in the methods of the invention. Alternatively, fresh or frozen tissue can be pressed against glass slides to form monolayers of cells known as touch preparations, which contain intact nuclei and do not suffer from the truncation artifact of sectioning. These cells may be fixed, e.g., in alcoholic solutions such as 100% ethanol or 3:1 methanol:acetic acid. Nuclei can also be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution such as formaldehyde.

7. Prescreening of Samples

Prior to detection, cell samples may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed. During pre-selection, cells from a biological sample can be placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes such as propidium iodide or 4,6-diamidino-2-phenylindole dihydrochloride (DAPI) usually following hybridization of probes to their target DNAs. Typically, neoplastic cells harbor nuclei that are enlarged, irregular in shape, and/or show a mottled staining pattern. Propidium iodide, typically used at a concentration of about 0.4 µg/ml to about 5 µg/ml, is a red-fluorescing DNA-specific dye that can be observed at an emission peak wavelength of 614 nm. DAPI, typically used at a concentration of about 125 ng/ml to about 1000 ng/ml is a blue fluorescing DNA-specific stain that can be observed at an emission peak wavelength of 452 nm. In this case, only those cells pre-selected for detection are subjected to counting for chromosomal losses and/or gains. Preferably, pre-selected cells on the order of at least 20, and more preferably at least 30-40, in number are chosen for assessing chromosomal losses and/or gains. Preselection of a suspicious region on a tissue section may be performed on a serial section stained by conventional means, such as H&E or PAP staining, and the suspect region marked by a pathologist or otherwise trained technician. The same region can then be located on the serial section stained by FISH and nuclei enumerated within that region. Within the marked region, enumeration may be limited to nuclei exhibiting abnormal characteristics as described above.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

8. Hybridization Pattern a. FISH

The hybridization pattern for the set of chromosomal probes to the target regions is detected and recorded for cells chosen for assessment of chromosomal losses and/or gains.

Hybridization is detected by the presence or absence of the particular signals generated by each of the chromosomal probes. The term "hybridization pattern" is intended to refer to the quantification of chromosomal losses/gains for those cells chosen for such assessment, relative to the number of the same in an evenly matched control sample, for each probe throughout a chosen cell sample. The quantification of losses/gains can include determinations that evaluate the ratio of one locus to another on the same or a different chromosome. Once the number of target regions within each cell is determined, as assessed by the number of regions showing hybridization to each probe, relative chromosomal gains and/or losses may be quantified.

The relative gain or loss for each probe is determined by comparing the number of distinct probe signals in each cell to the number expected in a normal cell, i.e., where the copy number should be two. Non-neoplastic cells in the sample, such as keratinocytes, fibroblasts, and lymphocytes, can be used as reference normal cells. More than the normal number of probe signals is considered a gain, and fewer than the normal number is considered a loss. Alternatively, a minimum number of signals per probe per cell can be required to consider the cell abnormal (e.g., 5 or more signals) Likewise for loss, a maximum number of signals per probe can be required to consider the cell abnormal (e.g., 0 signals, or one or fewer signals).

The percentages of cells with at least one gain and/or loss are to be recorded for each locus. A cell is considered abnormal if at least one of the identified genetic aberrations identified by a probe combination of the present disclosure is found in that cell. A sample may be considered positive for a gain or loss if the percentage of cells with the respective gain or loss exceeds the cutoff value for any probes used in an assay. Alternatively, two or more genetic aberrations can be required in order to consider the cell abnormal with the effect of increasing specificity. For example, wherein gains are indicative of increased risk of poor disease outcome in NSCLC, a sample is considered positive if it contains, for example, at least four cells showing gains of at least two or more probe-containing regions.

b. aCGH

Array CGH can be carried out in single-color or dual- or multi-color mode. In single-color mode, only the sample nucleic acids are labeled and hybridized to the nucleic acid array. Copy number differences can be detected by detecting a signal intensity at a particular target nucleic acid spot on the array that differs significantly from the signal intensity observed at one or more spots corresponding to one or more loci that are present in the sample nucleic acids at a normal copy number. To facilitate this determination, the array can include target elements for one or more loci that are not expected to show copy number difference(s) in patients at increased risk of poor disease outcome in NSCLC.

In dual- or multi-color mode, signal corresponding to each labeled collection of nucleic acids (e.g., sample nucleic acids and normal, reference nucleic acids) is detected at each target nucleic acid spot on the array. The signals at each spot can be compared, e.g., by calculating a ratio. For example, if the ratio of sample nucleic acid signal to reference nucleic acid signal exceeds 1, this indicates a gain in the sample nucleic acids at the locus corresponding to the target nucleic acid spot on the array. Conversely, if t if the ratio of sample nucleic acid signal to reference nucleic acid signal is less than 1, this indicates a loss in the sample nucleic acids at the corresponding locus.

9. Probe Combinations and Kits for use in Diagnostic and/or Prognostic Applications The invention includes highly specific and sensitive combinations of probes, as described herein, that can be used to predict disease outcome in NSCLC, with particular reference to stage I-II NSCLC, and kits for use in diagnostic, research, and prognostic applications. Kits include probe combinations and can also include reagents such as buffers and the like. The kits may include instructional materials containing directions (i.e., protocols) for the practice of the methods of this invention. While the instructional materials typically include written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

All publications cited herein are explicitly incorporated by reference.

EXAMPLES

The following examples are offered to illustrate, but not to limit the claimed invention.

Example 1

Analysis of NSCLC Patient Samples

Experimental Methods: Specimens. A total of 178 NSCLC clinically annotated samples were profiled for copy number alterations using high-density SNP genotyping microarrays (100K array set by Affymetrix). All samples were carefully dissected to maximize tumor/normal tissue ratio and verify histopathological type and stage. Only samples from patients with stage I and II samples were analyzed. All of these were from patients treated with surgical resection without any follow-up or neoadjuvant chemotherapy. Clinical information collected for each patient included race, age, date of birth, sex, clinical stage, pathological stage, location, surgical procedure (SP) date, histology, differentiation, diagnosis date, node positivity, smoking status, chemotherapy status, radiation status, recurrence status, recurrence date, recurrence location, time to recurrence, date of last follow up, status at the last follow up, alive/dead, overall survival and cause of death. Time to Recurrence (TTR) and Overall Survival (OS) were chosen as the parameters of outcome. Other clinical parameters (node status, stage, etc) were considered as confounding variables. Times to recurrence of lung cancer and the overall survival times were obtained from the patient charts.

Tables 2 and 3 provide the figures for Overall Survival and Total Time to Recurrence, respectively, for the patient cohort studied.

TABLE 2

OS

| Stage | deaths | alive (censored) | total |
|---|---|---|---|
| 1a | 6 | 25 | 31 |
| 1b | 6 | 40 | 46 |
| 2a | 0 | 1 | 1 |
| 2b | 7 | 17 | 24 |
| total | 19 | 83 | 102 |

TABLE 3

TTR

| Stage | recurred | recurrence free (censored) | total |
|---|---|---|---|
| 1a | 10 | 21 | 31 |
| 1b | 9 | 34 | 43 |
| 2a | 1 | 0 | 1 |
| 2b | 9 | 13 | 22 |
| total | 29 | 68 | 97 |

Copy number profiling. Approximately 30 mg tissue from each tumor were used to extract high molecular weight, genomic DNA using the Qiagen DNAeasy kit (Qiagen, Valencia, Calif.) following the instructions by the manufacturer. The quality of DNA was checked by agarose gel electrophoresis. Two hundred and fifty nanograms of DNA were processed for hybridization to each of the two microarrays comprising the Genechip Human Mapping 100K set (Matsuzaki H, Dong S, Loi H, et al. Genotyping over 100,000 SNPs on a pair of oligonucleotide arrays. Nat Methods 2004; 1:109-11) -arrays (Affymetrix, Inc., Santa Clara, Calif.), which covers 116,204 single-nucleotide polymorphism (SNP) loci in the human genome with a mean intermarker distance of 23.6 kb. The microarrays were processed according to recommendations of the manufacturer. Copy number was calculated by comparing the chip signal to the average of 48 normal female samples. Samples with normal tissue contamination were removed by QC.

Statistical Methods. Univariate analysis was used to test the following parameters as potential confounding factors: Pathological stage, Clinical stage, Smoking status, Age, Sex, Node status, Histology (adenocarcinoma vs squamous cell carcinoma). No significant effects were detected. In survival analysis, interaction of clinical stage and marker regions was tested. No copy number abnormalities had significant interaction with stage (FDR p value<0.05).

Results: Only patients with stage I-II disease were analyzed. Kaplan-Meier analysis was applied to the data to generate a Kaplan-Meier plot for each marker, showing the difference in OS and/or TTR between patients with and without amplification of a selected marker as indicated (i.e., a copy number gain of at least one), or showing the difference in OS and/or TTR between patients with and without deletion (i.e., a copy number loss of at least one) of the selected marker. The plots showed that copy number alterations (gain or loss) in the specified markers are associated with short OS and/or shorter TTR in NSCLC stage I-II patients. Table 4 lists overall survival data for several markers. (Markers for which data is shown in the bottom two rows (e.g., at starting position 70761833) are shared between different clinical stages).

TABLE 4

Overall Survival for markers on Chr1, Chr2, Chr6, Chr8, Chr11, Chr12, Chr17, and Chr19

| Stages | chrom | start.pos | length.seg | FDR | n.amp | mean.amp | n.SNP |
|---|---|---|---|---|---|---|---|
| 1a-2a | 2 | 147604021 | 3513659 | 0.0233 | 7 | 2.8516132 | 166 |
| | 2 | 159911944 | 1511940 | 0.0001 | 5 | 3.2498274 | 67 |
| | 2 | 200924525 | 3320890 | 0.0398 | 6 | 3.006085 | 79 |
| | 2 | 205893481 | 2160144 | 0.0075 | 5 | 2.9990652 | 101 |
| | 3 | 88399682 | 386599 | 0.0140 | 5 | 3.5534647 | 12 |
| | 6 | 36255222 | 423122 | 0.0347 | 6 | 2.9201916 | 8 |
| | 6 | 39088059 | 762306 | 0.0356 | 15 | 3.1071308 | 30 |
| | 6 | 123724457 | 11850520 | 0.0377 | 7 | 2.9452862 | 667 |
| | 8 | 4115551 | 55428 | 0.0126 | 7 | 2.8073117 | 19 |
| | 8 | 6895465 | 1889190 | 0.0166 | 7 | 3.0262839 | 36 |
| | 11 | 61374252 | 2935902 | 0.0004 | 9 | 3.2120357 | 46 |
| | 11 | 64310154 | 493823 | 0.0040 | 12 | 3.5343537 | 6 |
| | 11 | 64803977 | 880941 | 0.0004 | 7 | 3.6506583 | 9 |
| | 12 | 93683 | 1774306 | 0.0493 | 11 | 3.604318 | 50 |
| | 17 | 43477124 | 1455714 | 0.0219 | 7 | 3.1622542 | 24 |
| | 17 | 51532820 | 1678229 | 0.0054 | 10 | 3.1730034 | 54 |
| | 17 | 69173224 | 2131396 | 0.0304 | 23 | 3.1612824 | 32 |
| | 19 | 32693527 | 387442 | 0.0183 | 18 | 4.0913848 | 8 |
| | 19 | 33195577 | 113123 | 0.0459 | 22 | 3.841479 | 6 |
| | 19 | 34722418 | 921516 | 0.0299 | 27 | 4.1530261 | 20 |
| | 19 | 38853838 | 1895624 | 0.0085 | 24 | 3.895232 | 34 |
| | 19 | 57033283 | 5156456 | 0.0091 | 14 | 3.1469281 | 83 |
| 1b-2b | 1 | 109538586 | 1580066 | 0.0224 | 5 | 2.9805551 | 58 |
| | 6 | 70761833 | 382704 | 0.0116 | 17 | 3.2107404 | 28 |
| 1a-2b | 6 | 70761833 | 382704 | 0.0110 | 24 | 3.0754468 | 28 |

Table 5 lists the genes and miRNA's that are encoded by nucleotide sequences within each cancer outcome marker sequence. In any of the methods, the cancer outcome marker can be selected from among those listed in Table 5. Those markers designated "M1" through "M20" are each a region of chromosomal DNA, the amplification of which produces a copy number gain in the cancer outcome marker, wherein the copy number gain is associated with a poor disease outcome. Those markers designated "DM1" through "DM27" are each a region of chromosomal DNA, the deletion of which produces a copy number loss in the cancer outcome marker, wherein the copy number loss is associated with a poor disease outcome.

TABLE 5

Cancer outcome markers and corresponding genes and miRNA's

| ID No. | Cancer outcome marker | Genes and miRNA's |
|---|---|---|
| M1 | Chr 19, 34.7 Mb-35.6 Mb; | C19orf12; C19orf12; cyclin E1; PLEKHF1; POP4; and ZNF536 |
| M2 | Chr 19, 38.9-40.7 Mb; | ATP4A ATPase; CHST8, DMKN FAR1,2,3; FXYD1,3,5,7; GAPDHS; GPI; GPR42; GRAMD1A; HAMP; HPN; KCTD15 KIAA0355; KRTDAP; LGI4; LSM14A; LSR; MAG; PDCD2L; SAE2 SUMO1; SBSN; SCN1B; TMEM147,162; USF2; WTIP; and ZNF181,30,302,599,792 |
| M3 | Chr 17, 69.2-71.3 Mb; | ARMC7 (armadillo repeat containing 7); ATP5H ATP synthase (H+ transporting, mitochondrial F0 complex, subunit d); CASKIN2 (CASK interacting protein 2); CD300A (CD300a molecule); CD300C (CD300c molecule); CD300E (CD300e molecule); CD300LB (CD300 molecule-like family member b); CD300LF (CD300 molecule-like family member f); CDR2L (cerebellar degeneration-related protein 2-like); DNAI2 (dynein, axonemal, intermediate chain 2); (FADS6 fatty acid desaturase domain family, member 6); FDXR (ferredoxin reductase); GALK1 (galactokinase 1); GGA3 (golgi associated, gamma adaptin ear containing, ARF binding protein): GPR142 (G protein-coupled receptor 142); GPRC5C (G protein-coupled receptor, family C, group 5, member C); GRB2 (growth factor receptor-bound protein 2); GRIN2C (glutamate receptor, ionotropic, N-methyl D-aspartate 2C); H3F3B (H3 histone, family 3B (H3.3B)); HN1 (hematological and neurological expressed 1 ICT1 immature colon carcinoma transcript 1); ITGB4 (integrin, beta 4); KCTD2 (potassium channel tetramerisation domain containing 2); KIAA0195; KIF19 (kinesin family member 19); LLGL2 (lethal giant larvae homolog 2 (*Drosophila*)); LOC388419 (galectin-3-binding protein-like); MIF4GD (MIF4G domain containing); MRPS7 (mitochondrial ribosomal protein S7); NAT9 (N-acetyltransferase 9); NT5C (5',3'-nucleotidase, cytosolic); NUP85 (nucleoporin 85 kDa); OTOP2 (otopetrin 2); OTOP3 (otopetrin 3); RAB37 (RAB37, member RAS oncogene family); RECQL5 (RecQ protein-like 5); RPL38 ribosomal protein L38; SAP30BP (SAP30 binding protein); SLC16A5 (solute carrier family 16, member 5 (monocarboxylic acid transporter 6)); SLC25A19 (solute carrier family 25 (mitochondrial thiamine pyrophosphate carrier), member 19); SLC9A3R1 (solute carrier family 9 (sodium/hydrogen exchanger), member 3 regulator 1); SUMO2 (SMT3 suppressor of mif two 3 homolog 2 (*S. cerevisiae*)); TMEM104 (transmembrane protein 104); TTYH2 (tweety homolog 2 (*Drosophila*)); UNK (unkempt homolog (*Drosophila*)); and USH1G (Usher syndrome 1G (autosomal recessive) |
| M4 | Chr 6, 70.8-71.1 Mb; | COL19A1 (collagen, type XIX, alpha 1), and COL9A1 (collagen, type IX, alpha 1) |
| M5 | Chr 12, 93.7 kb-1.9 Mb; | ADIPOR2 (adiponectin receptor 2); B4GALNT3 (beta-1,4-N-acetyl-galactosaminyl transferase 3); CACNA2D4 (calcium channel, voltage-dependent, alpha 2/delta subunit 4); CCDC77 (coiled-coil domain containing 77); ERC1 (ELKS/RAB6-interacting/CAST family member 1); FBXL14 (F-box and leucine-rich repeat protein 14); HSN2 (hereditary sensory neuropathy, type II); IQSEC3 (IQ motif and Sec7 domain 3); JARID1A (jumonji, AT rich interactive domain 1A); LRTM2 (leucine-rich repeats and transmembrane domains 2); NINJ2 (ninjurin 2); RAD52 (RAD52 homolog (*S. cerevisiae*)); SLC6A12 (solute carrier family 6 (neurotransmitter transporter, betaine/GABA), member 12); SLC6A13 (solute carrier family 6 (neurotransmitter transporter, GABA), member 13); WNK1 (WNK lysine deficient protein kinase 1); and WNT5B (wingless-type MMTV integration site family, member 5B) |

TABLE 5-continued

Cancer outcome markers and corresponding genes and miRNA's

| ID No. | Cancer outcome marker | Genes and miRNA's |
|---|---|---|
| M6 | Chr 11, 64.3-64.8 Mb; | ARL2 (ADP-ribosylation factor-like 2); ATG2A ATG2 (autophagy related 2 homolog A (*S. cerevisiae*)); BATF2 (basic leucine zipper transcription factor, ATF-like 2; CAPN1 calpain 1, (mu/I) large subunit); CDC42BPG (CDC42 binding protein kinase gamma (DMPK-like)); CDCA5 (cell division cycle associated 5); EHD1 (EH-domain containing 1); FAU (Finkel-Biskis-Reilly murine sarcoma virus (FBR-MuSV) ubiquitously expressed); GPHA2 (glycoprotein hormone alpha 2);<br>MAP4K2 mitogen-activated protein kinase kinase kinase kinase 2<br>MEN1 multiple endocrine neoplasia I<br>MRPL49 mitochondrial ribosomal protein L49<br>NAALADL1 N-acetylated alpha-linked acidic dipeptidase-like 1<br>POLA2 polymerase (DNA directed), alpha 2 (70 kD subunit)<br>PPP2R5B protein phosphatase 2, regulatory subunit B', beta isoform<br>SAC3D1 SACS domain containing 1<br>SLC22A20 solute carrier family 22, member 20<br>SNX15 sorting nexin 15<br>SPDYC speedy homolog C (*Drosophila*)<br>SYVN1 synovial apoptosis inhibitor 1, synoviolin<br>TM7SF2 transmembrane 7 superfamily member 2<br>ZFPL1 zinc finger protein-like 1<br>ZNHIT2 zinc finger, HIT type 2;<br>hsa-mir-192; and<br>hsa-mir-194-2 |
| M7 | Chr 19, 57.0-62.2 Mb; | BIRC8 (baculoviral IAP repeat-containing 8); BRSK1 (BR serine/threonine kinase 1); CACNG6,7,8 calcium channel, voltage-dependent, gamma subunit 6, 7, 8<br>CCDC106 coiled-coil domain containing 106<br>CDC42EP5 CDC42 effector protein (Rho GTPase binding) 5<br>CNOT3 CCR4-NOT transcription complex, subunit 3<br>COX6B2 cytochrome c oxidase subunit VIb polypeptide 2 (testis)<br>DPRX divergent-paired related homeobox<br>EPN1 epsin 1<br>EPS8L1 EPS8-like 1<br>FCAR Fc fragment of IgA, receptor for<br>FIZ1 FLT3-interacting zinc finger 1<br>GALP galanin-like peptide<br>GP6 glycoprotein VI (platelet)<br>HSPBP1 hsp70-interacting protein<br>IL11 interleukin 11<br>ISOC2 isochorismatase domain containing 2<br>KIR2DL1, KIR2DL4, KIR2DS4 KIR3DL1, KIR3DL3, KIR3DX1 killer cell immunoglobulin-like receptor<br>LAIR1,2 leukocyte-associated immunoglobulin-like receptor 1, 2<br>LENG1,4,8,9 leukocyte receptor cluster (LRC) member 1, 4, 8, 9<br>LILRA2,3,4 leukocyte immunoglobulin-like receptor, subfamily A (with TM domain), member 2, 3, 4<br>LILRB1,2,3,4,5 leukocyte immunoglobulin-like receptor, subfamily B (with TM and ITIM domains), member 1, 2, 3, 4, 5<br>MYADM myeloid-associated differentiation marker<br>NAT14 N-acetyltransferase 14<br>NCR1 natural cytotoxicity triggering receptor 1<br>NDUFA3 NADH dehydrogenase (ubiquinone) 1 alpha subcomplex, 3, 9 kDa<br>NLRP2,4,5,7,8,9,11,12,13 NLR family, pyrin domain containing 2, 4, 5, 7, 8, 9, 11, 12, 13.<br>OSCAR osteoclast associated, immunoglobulin-like receptor<br>PEG3 paternally expressed 3<br>PPP1R12C protein phosphatase 1, regulatory (inhibitor) subunit 12C |

TABLE 5-continued

Cancer outcome markers and corresponding genes and miRNA's

| ID No. | Cancer outcome marker | Genes and miRNA's |
|---|---|---|
| | | PPP2R1A protein phosphatase 2 (formerly 2A), regulatory subunit A, alpha isoform<br>PRKCG protein kinase C, gamma<br>PRPF31 PRP31 pre-mRNA processing factor 31 homolog (S. cerevisiae)<br>PTPRH protein tyrosine phosphatase, receptor type, H<br>RDH13 retinol dehydrogenase 13 (all-trans/9-cis)<br>RPL28 ribosomal protein L28<br>RPS9 ribosomal protein S9<br>SAPS1 SAPS domain family, member 1<br>SUV420H2 suppressor of variegation 4-20 homolog 2 (Drosophila)<br>SYT5 synaptotagmin V<br>TFPT TCF3 (E2A) fusion partner (in childhood Leukemia)<br>TMC4 transmembrane channel-like 4<br>TMEM190 transmembrane protein 190<br>TMEM86B transmembrane protein 86B<br>TNNI3 troponin I type 3 (cardiac)<br>TNNT1 troponin T type 1 (skeletal, slow)<br>TSEN34 tRNA splicing endonuclease 34 homolog (S. cerevisiae)<br>TTYH1 tweety homolog 1 (Drosophila)<br>U2AF2 U2 small nuclear RNA auxiliary factor 2<br>UBE2S ubiquitin-conjugating enzyme E2S<br>VN1R2 vomeronasal 1 receptor 2<br>VN1R4 vomeronasal 1 receptor 4<br>VSTM1 V-set and transmembrane domain containing 1<br>ZNF28,160,320,321,331,347,350,415,432,444,468,470 zinc finger protein 28, 160, 320, 321, 331, 347, 350, 415, 432, 444, 468, 470; and miRNA's including<br>hsa-mir-643, hsa-mir-512-1, hsa-mir-512-2, hsa-mir-498, hsa-mir-520e, hsa-mir-515-1, hsa-mir-519e, hsa-mir-520f, hsa-mir-515-2, hsa-mir-519c, hsa-mir-520a, hsa-mir-526b, hsa-mir-519b, hsa-mir-525, hsa-mir-523, hsa-mir-518f, hsa-mir-520b, hsa-mir-518b, hsa-mir-526a-1, hsa-mir-520c, hsa-mir-518c, hsa-mir-524, hsa-mir-517a, hsa-mir-519d, hsa-mir-521-2, hsa-mir-520d, hsa-mir-517b, hsa-mir-520g, hsa-mir-516-3, hsa-mir-526a-2, hsa-mir-518e, hsa-mir-518a-1, hsa-mir-518d, hsa-mir-516-4, hsa-mir-518a-2, hsa-mir-517c, hsa-mir-520h, hsa-mir-521-1, hsa-mir-522, hsa-mir-519a-1, hsa-mir-527, hsa-mir-516-1, hsa-mir-516-2, hsa-mir-519a-2, hsa-mir-371, hsa-mir-372, hsa-mir-373, hsa-mir-516a-1, hsa-mir-516a-2, hsa-mir-516b-1, hsa-mir-516b-2, hsa-mir-517a-1, hsa-mir-517a-2, hsa-mir-520c-1, hsa-mir-520c-2 |
| M8 | Chr 6, 39.1-39.9 Mb; | C6orf64 (chromosome 6 open reading frame 64);<br>DNAH8 dynein, axonemal, heavy chain 8<br>GLP1R glucagon-like peptide 1 receptor<br>KCNK16 potassium channel, subfamily K, member 16<br>KCNK17 potassium channel, subfamily K, member 17<br>KCNK5 potassium channel, subfamily K, member 5<br>KIF6 kinesin family member 6. |
| M9 | Chr 11, 64.8-65.7 Mb; | BANF1 (barrier to autointegration factor 1);<br>CATSPER1 cation channel, sperm associated 1<br>CCDC85B coiled-coil domain containing 85B<br>CDC42EP2 CDC42 effector protein (Rho GTPase binding) 2<br>CFL1 cofilin 1 (non-muscle)<br>CST6 cystatin E/M<br>CTSW cathepsin W<br>DPF2 D4, zinc and double PHD fingers family 2<br>DRAP1 DR1-associated protein 1 (negative cofactor 2 alpha)<br>EFEMP2 EGF-containing fibulin-like extracellular matrix protein 2<br>EHBP1L1 EH domain binding protein 1-like 1<br>FAM89B family with sequence similarity 89, member B<br>FIBP fibroblast growth factor (acidic) intracellular binding protein<br>FOSL1 FOS-like antigen 1<br>FRMD8 FERM domain containing 8<br>GAL3ST3 galactose-3-O-sulfotransferase 3<br>HTATIP HIV-1 Tat interacting protein, 60 kDa. KCNK7 potassium channel, subfamily K, member 7 |

TABLE 5-continued

Cancer outcome markers and corresponding genes and miRNA's

| ID No. | Cancer outcome marker | Genes and miRNA's |
|---|---|---|
| | | LTBP3 latent transforming growth factor beta binding protein 3 |
| | | MAP3K11 mitogen-activated protein kinase kinase kinase 11 |
| | | MGC11102 hypothetical protein MGC11102 |
| | | MUS81 MUS81 endonuclease homolog (*S. cerevisiae*) |
| | | OVOL1 ovo-like 1 (*Drosophila*) |
| | | PACS1 phosphofurin acidic cluster sorting protein 1 |
| | | PCNXL3 pecanex-like 3 (*Drosophila*) |
| | | POLA2 polymerase (DNA directed), alpha 2 (70 kD subunit) |
| | | RELA v-rel reticuloendotheliosis viral oncogene homolog A, nuclear factor of kappa light polypeptide gene enhancer in B-cells 3, p65 (avian) |
| | | RNASEH2C ribonuclease H2, subunit C |
| | | SART1 squamous cell carcinoma antigen recognized by T cells |
| | | SCYL1 SCY1-like 1 (*S. cerevisiae*) |
| | | SF3B2 splicing factor 3b, subunit 2, 145 kDa |
| | | SIPA1 signal-induced proliferation-associated gene 1 |
| | | SLC25A45 solute carrier family 25, member 45 |
| | | SSSCA1 Sjogren syndrome/scleroderma autoantigen 1 |
| | | TIGD3 tigger transposable element derived 3 |
| | | TSGA10IP testis specific, 10 interacting protein |
| M10 | Chr 11, 61.4-64.3 Mb; | AHNAK (AHNAK nucleoprotein); |
| | | ASRGL1 asparaginase like 1 |
| | | B3GAT3 beta-1,3-glucuronyltransferase 3 (glucuronosyltransferase I) |
| | | BAD BCL2-antagonist of cell death |
| | | BEST1 bestrophin 1 |
| | | BSCL2 Bernardinelli-Seip congenital lipodystrophy 2 (seipin) |
| | | CCDC88B coiled-coil domain containing 88B |
| | | CHRM1 cholinergic receptor, muscarinic 1 |
| | | COX8A cytochrome c oxidase subunit 8A (ubiquitous) |
| | | DKFZP564J0863 DKFZP564J0863 protein |
| | | DKFZP566E164 DKFZP566E164 protein |
| | | DNAJC4 DnaJ (Hsp40) homolog, subfamily C, member 4 |
| | | EEF1G eukaryotic translation elongation factor 1 gamma |
| | | EML3 echinoderm microtubule associated protein like 3 |
| | | ESRRA estrogen-related receptor alpha |
| | | FADS2,3 fatty acid desaturase 2,3 |
| | | FKBP2 FK506 binding protein 2, 13 kDa |
| | | FLRT1 fibronectin leucine rich transmembrane protein 1 |
| | | FTH1 ferritin, heavy polypeptide 1 |
| | | GANAB glucosidase, alpha; neutral AB |
| | | GNG3 guanine nucleotide binding protein (G protein), gamma 3 |
| | | GPR137 G protein-coupled receptor 137 |
| | | HRASLS2,3,5 HRAS-like suppressor 2,3,5 |
| | | INCENP inner centromere protein antigens 135/155 kDa |
| | | INTS5 integrator complex subunit 5 |
| | | KCNK4 potassium channel, subfamily K, member 4 |
| | | LGALS12 lectin, galactoside-binding, soluble, 12 (galectin 12) |
| | | MACROD1 MACRO domain containing 1 |
| | | MARK2 MAP/microtubule affinity-regulating kinase 2 |
| | | MGC3196 hypothetical protein MGC3196 |
| | | MTA2 metastasis associated 1 family, member 2 |
| | | NAT11 N-acetyltransferase 11 |
| | | NRXN2 neurexin 2 |
| | | NUDT22 nudix (nucleoside diphosphate linked moiety X)-type motif 22 |
| | | NXF1 nuclear RNA export factor 1 |
| | | OTUB1 OTU domain, ubiquitin aldehyde binding 1 |
| | | PLCB3 phospholipase C, beta 3 (phosphatidylinositol-specific) |
| | | POLR2G polymerase (RNA) II (DNA directed) polypeptide G |
| | | PPP1R14B protein phosphatase 1, regulatory (inhibitor) subunit 14B |
| | | PRDX5 peroxiredoxin 5 |
| | | PYGM phosphorylase, glycogen; muscle (McArdle syndrome, glycogen storage disease type V) |

TABLE 5-continued

Cancer outcome markers and corresponding genes and miRNA's

| ID No. | Cancer outcome marker | Genes and miRNA's |
|---|---|---|
| | | RAB3IL1 RAB3A interacting protein (rabin3)-like 1
RARRES3 retinoic acid receptor responder (tazarotene induced) 3
RASGRP2 RAS guanyl releasing protein 2 (calcium and DAG-regulated)
RCOR2 REST corepressor 2
ROM1 retinal outer segment membrane protein 1
RPS6KA4 ribosomal protein S6 kinase, 90 kDa, polypeptide 4
RTN3 reticulon 3
SCGB1A1, 1D1, 1D2, 1D4, 2A1, 2A1 secretoglobin, family
SF1 splicing factor 1
SLC22A10, 11, 12, 6, 8, 9 solute carrier family 22 (organic anion/cation transporter) SLC3A2 solute carrier family 3 (activators of dibasic and neutral amino acid transport), member 2
STIP1 stress-induced-phosphoprotein 1 (Hsp70/Hsp90-organizing protein)
STX5 syntaxin 5
TAF6L TAF6-like RNA polymerase II, p300/CBP-associated factor (PCAF)-associated factor, 65 kDa
TRPT1 tRNA phosphotransferase 1
TTC9C tetratricopeptide repeat domain 9C
TUT1 terminal uridylyl transferase 1, U6 snRNA-specific
URP2 UNC-112 related protein 2
UST6 putative UST1-like organic anion transporter
VEGFB vascular endothelial growth factor B
WDR74 WD repeat domain 74; and
ZBTB3 zinc finger and BTB domain containing 3 |
| M11 | Chr 17, 51.5-53.2 Mb; | AKAP1 (A kinase (PRKA) anchor protein 1);
ANKFN1 (ankyrin-repeat and fibronectin type III domain containing 1);
C17orf67 chromosome 17 open reading frame 67
COIL coilin
DGKE diacylglycerol kinase, epsilon 64 kDa
MSI2 musashi homolog 2 (*Drosophila*)
NOG noggin
SCPEP1 serine carboxypeptidase 1; and
TRIM25 tripartite motif-containing 25 |
| M12 | Chr 17, 43.5-44.9 Mb; | hsa-mir-10a; hsa-mir-196a-1; ABI3 (ABI gene family, member 3); ATP5G1 (ATP synthase, H+ transporting, mitochondrial F0 complex, subunit C1 (subunit 9));
B4GALNT2 beta-1,4-N-acetyl-galactosaminyl transferase 2
CALCOCO2 calcium binding and coiled-coil domain 2
CBX1 chromobox homolog 1 (HP1 beta homolog *Drosophila*)
GIP gastric inhibitory polypeptide
GNGT2 guanine nucleotide binding protein (G protein), gamma transducing activity polypeptide 2
HOXB1,2,3,4,5,6,7,8,9,13 homeobox B1,2,3,4,5,6,7,8,9,13
IGF2BP1 insulin-like growth factor 2 mRNA binding protein 1
NFE2L1 nuclear factor (erythroid-derived 2)-like 1
NGFR nerve growth factor receptor (TNFR superfamily, member 16)
PHB prohibitin
PHOSPHO1 phosphatase, orphan 1
PRAC small nuclear protein PRAC
SKAP1 src kinase associated phosphoprotein 1
SNF8 SNF8, ESCRT-II complex subunit, homolog (*S. cerevisiae*)
SNX11 sorting nexin 11
TTLL6 tubulin tyrosine ligase-like family, member 6
UBE2Z (ubiquitin-conjugating enzyme E2Z); and
ZNF652 (zinc finger protein 652). |
| M13 | Chr 2, 147.6-151.1 Mb; | ACVR2A activin A receptor, type IIA; C2orf25 chromosome 2 open reading frame 25
EPC2 enhancer of polycomb homolog 2 (*Drosophila*)
KIF5C kinesin family member 5C
LOC130576 hypothetical protein LOC130576
LYPD6 LY6/PLAUR domain containing 6
MBD5 methyl-CpG binding domain protein 5 |

TABLE 5-continued

Cancer outcome markers and corresponding genes and miRNA's

| ID No. | Cancer outcome marker | Genes and miRNA's |
|---|---|---|
| M14 | Chr 6, 123.7-135.6 Mb; | ORC4L origin recognition complex, subunit 4-like (yeast)<br>RND3 Rho family GTPase 3<br>hsa-mir-588;<br>AKAP7 (A kinase (PRKA) anchor protein 7);<br>ALDH8A1 aldehyde dehydrogenase 8 family, member A1<br>ARG1 arginase, liver<br>ARHGAP18 Rho GTPase activating protein 18<br>CTGF connective tissue growth factor<br>ECHDC1 enoyl Coenzyme A hydratase domain containing 1<br>ENPP1,3 ectonucleotide pyrophosphatase/phosphodiesterase 1,3<br>EPB41L2 erythrocyte membrane protein band 4.1-like 2<br>EYA4 eyes absent homolog 4 (*Drosophila*)<br>HDDC2 HD domain containing 2<br>HEY2 hairy/enhancer-of-split related with YRPW motif 2<br>HINT3 histidine triad nucleotide binding protein 3<br>KIAA1913 KIAA1913<br>LAMA2 laminin, alpha 2 (merosin, congenital muscular dystrophy)<br>MED23 mediator complex subunit 23<br>MOXD1 monooxygenase, DBH-like 1<br>MYB v-myb myeloblastosis viral oncogene homolog (avian)<br>NCOA7 nuclear receptor coactivator 7<br>NKAIN2 Na+/K+ transporting ATPase interacting 2<br>OR2A4 olfactory receptor, family 2, subfamily A, member 4<br>PTPRK protein tyrosine phosphatase, receptor type, K.<br>RNF146 ring finger protein 146<br>RNF217 ring finger protein 217<br>RPS12 ribosomal protein S12<br>SAMD3 sterile alpha motif domain containing 3<br>SGK serum/glucocorticoid regulated kinase<br>SLC2A12 solute carrier family 2 (facilitated glucose transporter), member 12<br>STX7 syntaxin 7<br>TAAR1,2,5,6,8,9 trace amine associated receptor 1,2,5,6,8,9<br>TBPL1 TBP-like 1<br>TCF21 transcription factor 21<br>TPD52L1 tumor protein D52-like 1<br>TRDN triadin<br>TRMT11 tRNA methyltransferase 11 homolog (*S. cerevisiae*)); and<br>VNN1,2,3 (vanin 1,2,3). |
| M15 | Chr 8, 6.9-8.8 Mb; | CLDN23 claudin 23;<br>DEFA5 defensin, alpha 5, Paneth cell-specific;<br>DEFB103B defensin, beta 103B<br>DEFB104A defensin, beta 104A<br>DEFB104B defensin, beta 104B<br>DEFB105B defensin, beta 105B<br>DEFB106A defensin, beta 106A<br>DEFB106B defensin, beta 106B<br>DEFB107A defensin, beta 107A<br>DEFB107B defensin, beta 107B<br>DEFB4 defensin, beta 4<br>MFHAS1 malignant fibrous histiocytoma amplified sequence 1<br>PRAGMIN homolog of rat pragma of Rnd2<br>SPAG11A sperm associated antigen 11A; and<br>SPAG11B sperm associated antigen 11B |
| M16 | Chr 2, 159.9-161.4 Mb; | BAZ2B bromodomain adjacent to zinc finger domain, 2B;<br>CD302 CD302 molecule<br>ITGB6 integrin, beta 6<br>LY75 lymphocyte antigen 75<br>MARCH7 (membrane-associated ring finger (C3HC4) 7);<br>PLA2R1 (phospholipase A2 receptor 1, 180 kDa); and<br>RBMS1 (RNA binding motif, single stranded interacting protein 1). |

TABLE 5-continued

Cancer outcome markers and corresponding genes and miRNA's

| ID No. | Cancer outcome marker | Genes and miRNA's |
|---|---|---|
| M17 | Chr 2, 200.9-204.2 Mb; | ABI2 abl interactor 2; ALS2 amyotrophic lateral sclerosis 2 (juvenile) ALS2CR2, 4, 7, 8, 11, 12, 13 amyotrophic lateral sclerosis 2 (juvenile) chromosome region, candidate 2, 4, 7, 8, 11, 12, 13 AOX1 aldehyde oxidase 1 BMPR2 bone morphogenetic protein receptor, type II (serine/threonine kinase) BZW1 basic leucine zipper and W2 domains 1 CASP10 caspase 10, apoptosis-related cysteine peptidase CASP8 caspase 8, apoptosis-related cysteine peptidase CFLAR CASP8 and FADD-like apoptosis regulator CLK1 CDC-like kinase 1 CYP20A1 cytochrome P450, family 20, subfamily A, polypeptide 1 FAM126B family with sequence similarity 126, member B FZD7 frizzled homolog 7 (Drosophila) ICA1L islet cell autoantigen 1.69 kDa-like KCTD18 potassium channel tetramerisation domain containing 18 LOC26010 viral DNA polymerase-transactivated protein 6 MPP4 membrane protein, palmitoylated 4 (MAGUK p55 subfamily member 4). NBEAL1 neurobeachin-like 1 NDUFB3 NADH dehydrogenase (ubiquinone) 1 beta subcomplex, 3, 12 kDa NIF3L1 NIF3 NGG1 interacting factor 3-like 1 (S. pombe) NOP5/NOP58 nucleolar protein NOP5/NOP58 ORC2L origin recognition complex, subunit 2-like (yeast) PPIL3 peptidylprolyl isomerase (cyclophilin)-like 3 RAPH1 Ras association (RalGDS/AF-6) and pleckstrin homology domains 1 SGOL2 shugoshin-like 2 (S. pombe) SUMO1 SMT3 suppressor of mif two 3 homolog 1 (S. cerevisiae) TRAK2 trafficking protein, kinesin binding 2; and WDR12 (WD repeat domain 12) |
| M18 | Chr 6, 36.3-36.7 Mb; | BRPF3 (bromodomain and PHD finger containing, 3) DKFZp779B1540 hypothetical protein DKFZp779B1540 ETV7 ets variant gene 7 (TEL2 oncogene) KCTD20 potassium channel tetramerisation domain containing 20 PNPLA1 patatin-like phospholipase domain containing 1 PXT1 peroxisomal, testis specific 1 SFRS3 splicing factor, arginine/serine-rich 3; and STK38 (serine/threonine kinase 38) |
| M19 | Chr 2, 205.9-208.1 Mb; and | ADAM23 (ADAM metallopeptidase domain 23); CPO carboxypeptidase O; DYTN dystrotelin EEF1B2 eukaryotic translation elongation factor 1 beta 2 FASTKD2 FAST kinase domains 2 FLJ20309 hypothetical protein FLJ20309 GPR1 G protein-coupled receptor 1 KLF7 Kruppel-like factor 7 (ubiquitous) MDH1B malate dehydrogenase 1B, NAD (soluble) NDUFS1 NADH dehydrogenase (ubiquinone) Fe—S protein 1, 75 kDa (NADH-coenzyme Q reductase) NRP2 neuropilin 2 PARD3B par-3 partitioning defective 3 homolog B (C. elegans) ZDBF2 (zinc finger, DBF-type containing 2); and HCG_1657980 hCG1657980 |
| M20 | Chr 1, 109.5-111.1 Mb. | hsa-mir-197; AHCYL1 S-adenosylhomocysteine hydrolase-like 1); ALX3 aristaless-like homeobox 3 AMIGO1 adhesion molecule with Ig-like domain 1 AMPD2 adenosine monophosphate deaminase 2 (isoform L) ATXN7L2 ataxin 7-like 2 CELSR2 cadherin, EGF LAG seven-pass G-type receptor 2 (flamingo homolog, Drosophila) CSF1 colony stimulating factor 1 (macrophage) CYB561D1 cytochrome b-561 domain containing 1 EPS8L3 EPS8-like 3 |

TABLE 5-continued

Cancer outcome markers and corresponding genes and miRNA's

| ID No. | Cancer outcome marker | Genes and miRNA's |
|---|---|---|
| | | FAM40A family with sequence similarity 40, member A |
| | | GNAI3 guanine nucleotide binding protein (G protein), alpha inhibiting activity polypeptide 3 |
| | | GNAT2 guanine nucleotide binding protein (G protein), alpha transducing activity polypeptide 2 |
| | | GPR61 G protein-coupled receptor 61 |
| | | GSTM1,M2,M3,M4,M5 glutathione S-transferase M1, M2 (muscle), M3 (brain), M4, M5 |
| | | HBXIP hepatitis B virus x interacting protein |
| | | KCNA2,3,4,10 potassium voltage-gated channel, shaker-related subfamily, member 2,3,4,10; KIAA1324 KIAA1324 |
| | | MYBPHL myosin binding protein H-like |
| | | PROK1 prokineticin 1 |
| | | PSMA5 proteasome (prosome, macropain) subunit, alpha type, 5 |
| | | PSRC1 proline/serine-rich coiled-coil 1 |
| | | RBM15 RNA binding motif protein 15 |
| | | SARS seryl-tRNA synthetase |
| | | SLC16A4 solute carrier family 16, member 4 (monocarboxylic acid transporter 5) |
| | | SLC6A17 solute carrier family 6, member 17 |
| | | SORT1 sortilin 1 |
| | | SYPL2 synaptophysin-like 2 |
| | | UBL4B (ubiquitin-like 4B) |
| DM1 | Chr 5, 62.9-67.8 Mb | ADAMTS6 ADAM metallopeptidase with thrombospondin type 1 motif, 6 |
| | | CD180 CD180 molecule |
| | | CENPK centromere protein K |
| | | ERBB2IP erbb2 interacting protein |
| | | FLJ13611 hypothetical protein FLJ13611 |
| | | HTR1A 5-hydroxytryptamine (serotonin) receptor 1A |
| | | MAST4 microtubule associated serine/threonine kinase family member 4 |
| | | NLN neurolysin (metallopeptidase M3 family) |
| | | P18SRP P18SRP protein |
| | | PIK3R1 phosphoinositide-3-kinase, regulatory subunit 1 (p85 alpha) |
| | | PPWD1 peptidylprolyl isomerase domain and WD repeat containing 1 |
| | | RGS7BP regulator of G-protein signaling 7 binding protein |
| | | RNF180 ring finger protein 180 |
| | | SDCCAG10 serologically defined colon cancer antigen 10 |
| | | SFRS12 splicing factor, arginine/serine-rich 12 |
| | | SGTB small glutamine-rich tetratricopeptide repeat (TPR)-containing, beta0; and |
| | | TRIM23 tripartite motif-containing 23. |
| DM2 | Chr 5, 53.3-53.8 Mb | ARL15 (ADP-ribosylation factor-like 15); HSPB3 (heat shock 27 kDa protein 3) and hsa-miR-581. |
| DM3 | Chr 4, 105.8-107.2 Mb | FLJ20184 (hypothetical protein FLJ20184); GSTCD (glutathione S-transferase, C-terminal domain containing); |
| | | INTS12 integrator complex subunit 12 |
| | | KIAA1546 KIAA1546 |
| | | MGC16169 hypothetical protein MGC16169 |
| | | NPNT (nephronectin); and |
| | | PPA2 pyrophosphatase (inorganic) 2. |
| DM4 | Chr 16, 45.8-46.3 Mb | ITFG1 (integrin alpha FG-GAP repeat containing 1) and PHKB (phosphorylase kinase, beta). |
| DM5 | Chr 5, 50.7-52.0 Mb | ISL1 (ISL LIM homeobox). |
| DM6 | Chr 5, 94.2-96.1 Mb | ARSK (arylsulfatase family, member K); |
| | | CAST (calpastatin); |
| | | ELL2 (elongation factor, RNA polymerase II, 2); |
| | | FAM81B family with sequence similarity 81, member B |
| | | GLRX glutaredoxin (thioltransferase) |
| | | GPR150 G protein-coupled receptor 150 |
| | | KIAA0372 KIAA0372 |
| | | MCTP1 multiple C2 domains, transmembrane 1 |
| | | PCSK1 proprotein convertase subtilisin/kexin type 1 |
| | | RFESD (Rieske (Fe—S) domain containing) |
| | | RHOBTB3 Rho-related BTB domain containing 3 |
| | | SPATA9 (spermatogenesis associated 9); and |
| | | hsa-miR-583. |

TABLE 5-continued

Cancer outcome markers and corresponding genes and miRNA's

| ID No. | Cancer outcome marker | Genes and miRNA's |
|---|---|---|
| DM7 | Chr 9, 36.1-37.0 Mb | C9orf19 chromosome 9 open reading frame 19<br>CCIN calicin<br>CLTA clathrin, light chain (Lca)<br>GNE glucosamine (UDP-N-acetyl)-2-epimerase/N-acetylmannosamine kinase<br>MELK maternal embryonic leucine zipper kinase<br>PAX5 paired box 5<br>RECK reversion-inducing-cysteine-rich protein with kazal motifs<br>RNF38 ring finger protein 38. |
| DM8 | Chr 5, 94.2-96.1 Mb | ARSK arylsulfatase family, member K<br>CAST calpastatin<br>ELL2 elongation factor, RNA polymerase II, 2<br>FAM81B family with sequence similarity 81, member B<br>GLRX glutaredoxin (thioltransferase)<br>GPR150 G protein-coupled receptor 150<br>KIAA0372 KIAA0372<br>MCTP1 multiple C2 domains, transmembrane 1<br>PCSK1 proprotein convertase subtilisin/kexin type 1<br>RFESD Rieske (Fe—S) domain containing<br>RHOBTB3 Rho-related BTB domain containing 3<br>SPATA9 spermatogenesis associated |
| DM9 | Chr14, 51.1-52.8 Mb | C14orf166 chromosome 14 open reading frame 166;<br>DDHD1 DDHD domain containing 1<br>ERO1L ERO1-like (*S. cerevisiae*)<br>FRMD6 FERM domain containing 6<br>GNG2 guanine nucleotide binding protein (G protein), gamma 2<br>GNPNAT1 glucosamine-phosphate N-acetyltransferase 1<br>GPR137C G protein-coupled receptor 137C<br>NID2 nidogen 2 (osteonidogen)<br>PLEKHC1 pleckstrin homology domain containing, family C (with FERM domain) member 1<br>PSMC6 proteasome (prosome, macropain) 26S subunit, ATPase, 6<br>PTGDR prostaglandin D2 receptor (DP)<br>PTGER2 prostaglandin E receptor 2 (subtype EP2), 53 kDa<br>STYX serine/threonine/tyrosine interacting protein<br>TXNDC16 thioredoxin domain containing 16. |
| DM10 | Chr 14, 61.5-68.6 Mb | ACTN1 actinin, alpha 1<br>AKAP5 A kinase (PRKA) anchor protein 5<br>ARG2 arginase, type II<br>ATP6V1D ATPase, H+ transporting, lysosomal 34 kDa, V1 subunit D<br>C14orf50 chromosome 14 open reading frame 50<br>C14orf54 chromosome 14 open reading frame 54<br>C14orf83 chromosome 14 open reading frame 83<br>CHURC1 churchill domain containing 1<br>EIF2S1 eukaryotic translation initiation factor 2, subunit 1 alpha, 35 kDa<br>ESR2 estrogen receptor 2 (ER beta)<br>FLJ39779 FLJ39779 protein<br>FNTB farnesyltransferase, CAAX box, beta<br>FUT8 fucosyltransferase 8 (alpha (1,6) fucosyltransferase)<br>GPHB5 glycoprotein hormone beta 5<br>GPHN gephyrin<br>GPX2 glutathione peroxidase 2 (gastrointestinal)<br>HSPA2 heat shock 70 kDa protein 2<br>KCNH5 potassium voltage-gated channel, subfamily H (eag-related), member 5<br>MAX MYC associated factor X<br>MPP5 membrane protein, palmitoylated 5 (MAGUK p55 subfamily member 5)<br>MTHFD1 methylenetetrahydrofolate dehydrogenase (NADP+ dependent) 1, methenyltetrahydrofolate cyclohydrolase, formyltetrahydrofolate synthetase<br>PIGH phosphatidylinositol glycan anchor biosynthesis, class H<br>PLEK2 pleckstrin 2<br>PLEKHG3 pleckstrin homology domain containing, family G (with RhoGef domain) member 3<br>PLEKHH1 pleckstrin homology domain containing, family H (with MyTH4 domain) member 1 |

TABLE 5-continued

Cancer outcome markers and corresponding genes and miRNA's

| ID No. | Cancer outcome marker | Genes and miRNA's |
|---|---|---|
| | | PPP2R5E protein phosphatase 2, regulatory subunit B', epsilon isoform.<br>RAB15 RAB15, member RAS oncogene family<br>RAD51L1 RAD51-like 1 (*S. cerevisiae*)<br>RDH11 retinol dehydrogenase 11 (all-trans/9-cis/11-cis)<br>RDH12 retinol dehydrogenase 12 (all-trans/9-cis/11-cis)<br>RHOJ ras homolog gene family, member J<br>SGPP1 sphingosine-1-phosphate phosphatase 1<br>SPTB spectrin, beta, erythrocytic (includes spherocytosis, clinical type I)<br>SYNE2 spectrin repeat containing, nuclear envelope 2<br>SYT16 synaptotagmin XVI<br>VTI1B vesicle transport through interaction with t-SNAREs homolog 1B (yeast)<br>WDR22 WD repeat domain 22<br>WDR89 WD repeat domain 89<br>ZBTB1 zinc finger and BTB domain containing 1<br>ZBTB25 zinc finger and BTB domain containing 25<br>ZFP36L1 zinc finger protein 36, C3H type-like 1<br>ZFYVE26 zinc finger, FYVE domain containing 26 and hsa-miR-625. |
| DM11 | Chr 9, 28.1 Mb | LINGO2 (leucine rich repeat and Ig domain containing 2). |
| DM12 | Chr 4, 43.7-44.2 Mb | KCTD8 (potassium channel tetramerisation domain containing 8). |
| DM13 | Chr 5, 60.8-62.9 Mb | DIMT1L DIM1 dimethyladenosine transferase 1-like (*S. cerevisiae*)<br>FLJ37543 hypothetical protein FLJ37543<br>IPO11 importin 11<br>ISCA1L iron-sulfur cluster assembly 1 homolog (*S. cerevisiae*)-like<br>KIF2A kinesin heavy chain member 2A. |
| DM14 | Chr 3, 120.0-121.1 Mb | ADPRH ADP-ribosylarginine hydrolase;<br>B4GALT4 UDP-Gal:betaGlcNAc beta 1,4-galactosyltransferase, polypeptide 4<br>C3orf1 chromosome 3 open reading frame 1<br>C3orf15 chromosome 3 open reading frame 15<br>C3orf30 chromosome 3 open reading frame 30<br>CD80 CD80 molecule<br>CDGAP Cdc42 GTPase-activating protein<br>COX17 COX17 cytochrome c oxidase assembly homolog (*S. cerevisiae*)<br>GSK3B glycogen synthase kinase 3 beta<br>IGSF11 immunoglobulin superfamily, member 11<br>KTELC1 KTEL (Lys-Tyr-Glu-Leu) containing 1<br>NR1I2 nuclear receptor subfamily 1, group I, member 2<br>PLA1A phospholipase A1 member A<br>POPDC2 popeye domain containing 2<br>TMEM39A transmembrane protein 39A; and<br>UPK1B uroplakin 1B. |
| DM15 | Chr 4, 46.2-48.0 Mb | CLDN23 claudin 23;<br>DEFA5 defensin, alpha 5, Paneth cell-specific;<br>DEFB103B defensin, beta 103B<br>DEFB104A defensin, beta 104A<br>DEFB104B defensin, beta 104B<br>DEFB105B defensin, beta 105B<br>DEFB106A defensin, beta 106A<br>DEFB106B defensin, beta 106B<br>DEFB107A defensin, beta 107A<br>DEFB107B defensin, beta 107B<br>DEFB4 defensin, beta 4<br>MFHAS1 malignant fibrous histiocytoma amplified sequence 1<br>PRAGMIN homolog of rat pragma of Rnd2<br>SPAG11A sperm associated antigen 11A; and<br>SPAG11B sperm associated antigen 11B. |
| DM16 | Chr 14, 38.9-40.0 Mb | FBXO33 (F-box protein 33). |
| DM17 | Chr 4, 44.2-44.6 Mb | GNPDA2 (glucosamine-6-phosphate deaminase 2);<br>GUF1 (GUF1 GTPase homolog (*S. cerevisiae*)); and<br>YIPF7 (Yip1 domain family, member 7). |
| DM18 | Chr 2, 213.7-214.3 Mb | IKZF2 IKAROS family zinc finger 2 (Helios)<br>SPAG16 sperm associated antigen 16. |
| DM19 | Chr14, 43.9-46.6 Mb | C14orf106 chromosome 14 open reading frame 106<br>C14orf155 chromosome 14 open reading frame 155<br>C14orf28 chromosome 14 open reading frame 28<br>FANCM Fanconi anemia, complementation group M |

TABLE 5-continued

Cancer outcome markers and corresponding genes and miRNA's

| ID No. | Cancer outcome marker | Genes and miRNA's |
|---|---|---|
|  |  | FKBP3 FK506 binding protein 3, 25 kDa |
|  |  | KIAA0423 KIAA0423 |
|  |  | KLHL28 kelch-like 28 (*Drosophila*) |
|  |  | MDGA2 MAM domain containing glycosylphosphatidylinositol anchor 2 |
|  |  | PRPF39 PRP39 pre-mRNA processing factor 39 homolog (*S. cerevisiae*) |
|  |  | RPL10L ribosomal protein L10-like. |
| DM20 | Chr 14, 27.6-28.6 Mb | FOXG1 (forkhead box G1). |
| DM21 | Chr 3, 98.0-98.3 Mb | EPHA6 (EPH receptor A6). |
| DM22 | Chr14, 55.2-60.0 Mb | ACTR10 actin-related protein 10 homolog (*S. cerevisiae*) |
|  |  | ARID4A AT rich interactive domain 4A (RBP1-like) |
|  |  | C14orf100 chromosome 14 open reading frame 100 |
|  |  | C14orf101 chromosome 14 open reading frame 101 |
|  |  | C14orf105 chromosome 14 open reading frame 105 |
|  |  | C14orf108 chromosome 14 open reading frame 108 |
|  |  | C14orf135 chromosome 14 open reading frame 135 |
|  |  | C14orf149 chromosome 14 open reading frame 149 |
|  |  | C14orf37 chromosome 14 open reading frame 37 |
|  |  | C14orf39 chromosome 14 open reading frame 39 |
|  |  | DAAM1 dishevelled associated activator of morphogenesis 1 |
|  |  | DACT1 dapper, antagonist of beta-catenin, homolog 1 (*Xenopus laevis*) |
|  |  | DHRS7 dehydrogenase/reductase (SDR family) member 7 |
|  |  | EXOC5 exocyst complex component 5 |
|  |  | GPR135 G protein-coupled receptor 135 |
|  |  | KIAA0586 KIAA0586 |
|  |  | NAT12 N-acetyltransferase 12 |
|  |  | OTX2 orthodenticle homeobox 2 |
|  |  | PELI2 pellino homolog 2 (*Drosophila*) |
|  |  | PPM1A protein phosphatase 1A (formerly 2C), magnesium-dependent, alpha isoform |
|  |  | PSMA3 proteasome (prosome, macropain) subunit, alpha type, 3 |
|  |  | RTN1 reticulon 1 |
|  |  | SLC35F4 solute carrier family 35, member F4 |
|  |  | TIMM9 translocase of inner mitochondrial membrane 9 homolog (yeast) |
|  |  | UNQ9438 TIMM. |
| DM23 | Chr14, 48.7-51.1 Mb | ABHD12B abhydrolase domain containing 12B |
|  |  | ARF6 ADP-ribosylation factor 6 |
|  |  | ATP5S ATP synthase, H+ transporting, mitochondrial F0 complex, subunit s (factor B) |
|  |  | C14orf104 chromosome 14 open reading frame 104 |
|  |  | C14orf138 chromosome 14 open reading frame 138 |
|  |  | CDKL1 cyclin-dependent kinase-like 1 (CDC2-related kinase) |
|  |  | FRMD6 FERM domain containing 6 |
|  |  | KLHDC1 kelch domain containing 1 |
|  |  | KLHDC2 kelch domain containing 2 |
|  |  | L2HGDH L-2-hydroxyglutarate dehydrogenase |
|  |  | LOC196913 hypothetical protein LOC196913 |
|  |  | LOC283551 hypothetical protein LOC283551 |
|  |  | MAP4K5 mitogen-activated protein kinase kinase kinase kinase 5 |
|  |  | MGAT2 mannosyl (alpha-1,6-)-glycoprotein beta-1,2-N-acetylglucosaminyltransferase |
|  |  | NIN ninein (GSK3B interacting protein) |
|  |  | POLE2 polymerase (DNA directed), epsilon 2 (p59 subunit) |
|  |  | PPIL5 peptidylprolyl isomerase (cyclophilin)-like 5 |
|  |  | PYGL phosphorylase, glycogen; liver (Hers disease, glycogen storage disease type VI) |
|  |  | RPL36AL ribosomal protein L36a-like |
|  |  | RPS29 ribosomal protein S29. |
| DM24 | Chr 4, 81.4-83.2 Mb | BMP3 bone morphogenetic protein 3 (osteogenic) |
|  |  | C4orf22 chromosome 4 open reading frame 22 |
|  |  | FGF5 fibroblast growth factor 5 |
|  |  | PRKG2 protein kinase, cGMP-dependent, type II |
|  |  | RASGEF1B RasGEF domain family, member 1B. |
| DM25 | Chr 10, 51.9-54.2 Mb | ACF apobec-1 complementation factor |
|  |  | ASAH2B N-acylsphingosine amidohydrolase (non-lysosomal ceramidase) 2B |

TABLE 5-continued

Cancer outcome markers and corresponding genes and miRNA's

| ID No. | Cancer outcome marker | Genes and miRNA's |
|---|---|---|
|  |  | CSTF2T cleavage stimulation factor, 3' pre-RNA, subunit 2, 64 kDa, tau variant<br>DKK1 dickkopf homolog 1 (*Xenopus laevis*)<br>MBL2 mannose-binding lectin (protein C) 2, soluble (opsonic defect)<br>PRKG1 protein kinase, cGMP-dependent, type I<br>SGMS1 sphingomyelin synthase 1<br>hsa-miR-605. |
| DM26 | Chr 5, 55.2-58.6 Mb | ANKRD55 ankyrin repeat domain 55<br>C5orf29 chromosome 5 open reading frame 29<br>C5orf35 chromosome 5 open reading frame 35<br>DKFZp686D0972 similar to RIKEN cDNA 4732495G21 gene<br>GPBP1 GC-rich promoter binding protein 1<br>IL31RA interleukin 31 receptor A<br>IL6ST interleukin 6 signal transducer (gp130, oncostatin M receptor)<br>MAP3K1 mitogen-activated protein kinase kinase kinase 1<br>MIER3 mesoderm induction early response 1, family member 3<br>PDE4D phosphodiesterase 4D, cAMP-specific (phosphodiesterase E3 dunce homolog, *Drosophila*)<br>PLK2 polo-like kinase 2 (*Drosophila*)<br>RAB3C RAB3C, member RAS oncogene family. |
| DM27 | Chr 5, 67.8-68.5 Mb. | CCNB1 (cyclin B1) and SLC30A5 (solute carrier family 30 (zinc transporter), member 5). |

Table 6 lists the coordinates for each cancer outcome marker, using the same reference numerals listed in Table 5. All coordinates are based on human genome assembly hg18 (NCBI Build 36). Markers were prioritized in importance and assigned a reference numeral in descending order of importance. In other words, M1 refers to the amplification marker of highest priority, while M20 refers to the lowest priority marker, and DM1 refers to the deletion marker of highest priority, while DM27 refers to the deletion marker of lowest priority. For amplification markers (M1-M20), the following factors were considered in prioritizing the markers: a) the frequency that the marker was amplified among patients; b) the degree of amplification of the marker when amplified; and c) whether the marker contains genes with a known association to cancer. For deletion markers (DM1-DM27), the same factors a) and c) were considered ((b) was not comparably applicable because the "degree of deletion" is limited by the fact that only two copies can be deleted).

TABLE 6

| MarkerID | chrom | start.pos | end.pos |
|---|---|---|---|
| M1 | chr19 | 34722418 | 35643933 |
| M2 | chr19 | 38853838 | 40749461 |
| M3 | chr17 | 69173224 | 71304619 |
| M4 | chr6 | 70761833 | 71144537 |
| M5 | chr12 | 93683 | 1867988 |
| M6 | chr11 | 64310154 | 64803976 |
| M7 | chr19 | 57033283 | 62189738 |
| M8 | chr6 | 39088059 | 39850364 |
| M9 | chr11 | 64803977 | 65684917 |
| M10 | chr11 | 61374252 | 64310153 |
| M11 | chr17 | 51532820 | 53211048 |
| M12 | chr17 | 43477124 | 44932837 |
| M13 | chr2 | 147604021 | 151117679 |
| M14 | chr6 | 123724457 | 135574976 |
| M15 | chr8 | 6895465 | 8784654 |
| M16 | chr2 | 159911944 | 161423883 |
| M17 | chr2 | 200924525 | 204245414 |
| M18 | chr6 | 36255222 | 36678343 |
| M19 | chr2 | 205893481 | 208053624 |
| M20 | chr1 | 109538586 | 111118652 |
| DM1 | chr9 | 36056899 | 36988415 |
| DM2 | chr4 | 105818261 | 107238628 |
| DM3 | chr5 | 53264432 | 53790965 |
| DM4 | chr16 | 45791880 | 46313827 |
| DM5 | chr5 | 50706878 | 52008065 |
| DM6 | chr5 | 94204208 | 96112445 |
| DM7 | chr5 | 62942847 | 67798156 |
| DM9 | chr14 | 51108156 | 52752331 |
| DM10 | chr14 | 61456273 | 68632720 |
| DM11 | chr9 | 28057491 | 28114180 |
| DM12 | chr4 | 43689020 | 44161565 |
| DM13 | chr5 | 60797829 | 62942846 |
| DM14 | chr3 | 119993321 | 121112610 |
| DM15 | chr4 | 46246303 | 47955581 |
| DM16 | chr14 | 38939630 | 40021400 |
| DM17 | chr4 | 44161566 | 44606114 |
| DM18 | chr2 | 213677020 | 214308243 |
| DM19 | chr14 | 43899026 | 46591909 |
| DM20 | chr14 | 27646449 | 28630571 |
| DM21 | chr3 | 97988751 | 98257089 |
| DM22 | chr14 | 55249852 | 60045332 |
| DM23 | chr14 | 48734855 | 51108156 |
| DM24 | chr4 | 81371219 | 83187388 |
| DM25 | chr10 | 51929419 | 54199330 |
| DM26 | chr5 | 55221121 | 58648144 |
| DM27 | chr5 | 67798156 | 68516077 |

Unlike previously identified predictors (expression signatures), the biomarkers represent DNA gains and losses (stable events measurable by FISH). FISH probes can be used to enable validation/use of the markers, and the markers are strong candidates for use as stratification biomarkers in clinical trials. They can be used for example to define molecular subgroups of disease with distinct outcomes. As such they are likely to correlate with drug response.

These data indicate that use of genomic copy number assessment of the genetic markers measured by FISH, and with use of an appropriate classifier, is of prognostic importance in early stage NSCLC. The classifier was able to produce statistically significant classification of patients who had been treated with surgery without neoadjuvant or follow-up chemotherapy into favorable and unfavorable recurrence categories. No present clinical in vitro diagnostic assay provides this capability. Thus, FISH assays to the listed markers performed on early stage NSCLC biopsy specimens or resected tumors appear valuable in decisions related to adjuvant therapy.

Example 2

Validation of Prognostic Markers Using a Korean Sample Set

To validate forty-six (46) of the biomarkers that correlated with the clinical outcome of low stage NSCLC patients, an additional set of low stage NSCLC tumor tissues was collected from the Samsung Cancer Center in Korea, together with associated clinical outcome information.

All samples were carefully dissected to maximize tumor/normal tissue ratio and verify histopathological type and stage. Only samples from patients with stage I and II samples were analyzed. All of these were from patients treated with surgical resection without any follow-up or neoadjuvant chemotherapy. Clinical information collected for each patient included age, sex, clinical stage, pathological stage, location, histology, differentiation, smoking status, chemotherapy status, radiation status, recurrence status, recurrence date, recurrence location, brain metastasis status, time to recurrence, date of last follow up, status at the last follow up, alive/dead, overall survival and cause of death. Time to Recurrence (TTR) and Overall Survival (OS) were chosen as the parameters of outcome. Other clinical parameters (node status, stage, etc) were considered as confounding variables. Times to recurrence of lung cancer and the overall survival times were obtained from the patient charts. Tables 7 and 8 provide the figures for Overall Survival and Total Time to Recurrence, respectively, for the patient cohort studied.

TABLE 7

| | OS | | |
|---|---|---|---|
| Stage | deaths | Alive (censored) | total |
| 1a | 0 | 10 | 10 |
| 1b | 22 | 33 | 55 |
| 2a | 0 | 0 | 0 |
| 2b | 6 | 2 | 8 |
| Total | 28 | 45 | 73 |

TABLE 8

| | TTR | | |
|---|---|---|---|
| Stage | recurred | Recurrence free (censored) | total |
| 1a | 0 | 10 | 10 |
| 1b | 24 | 31 | 55 |
| 2a | 0 | 0 | 0 |
| 2b | 6 | 2 | 8 |
| total | 30 | 43 | 73 |

The samples were processed, DNA extracted, amplified and hybridized to Affymetrix SNP 6.0 arrays (Affymetrix, Inc., Santa Clara, Calif.) which contains more than 906,600 single nucleotide polymorphisms (SNPs) and more than 946,000 probes for the detection of copy number variation with a median intermarker distance over all 1.8 million SNP and copy number markers combined of less than 700 bases. The microarrays were processed according to recommendations of the manufacturer (Affymetrix). Copy number of these tumors was calculated by comparing to a HapMap set of 270 normal controls. The copy number was segmented using Partek software 6.09.0310.

The average copy number of the validation set showed a pattern similar to the previous training data set, but with a much higher density. To compare the average copy number pattern between training and validating data set, the log transformed copy numbers of each marker were averaged across all samples in the training and testing sets, where 0 represented the normal two copies. Average gain or loss of copy numbers, respectively, was shown to be consistent with the previous training data set.

The validation data presented in this example is based on eighteen (18) times greater the coverage of SNPs and CNV markers as compared to the 100K microarray data generated and used to identify the diagnostic markers, and therefore more small scale copy number changing events could be identified. Therefore, instead of calculating the copy number of each biomarker, the copy number of each gene within these biomarkers was calculated, and then correlated to the Overall Survival or Time to Recurrence of the patients.

Sixty-one (61) genes in total, in six (6) different markers were validated with the criterion of p-value by logrank test below 0.05. The genes are listed in Table 9 with significant p-values shown in bold and italics. FIGS. 62-162 are Kaplan-Meier plots showing either the overall survival (OS) or the time to recurrence (TTR) in days for the 73 patient cohort, classified by presence or absence of a copy number gain in the particular gene as indicated on each plot. As with the Kaplan-Meier plots of FIGS. 1-60, the x-axis represents time in days, and the y-axis the probability of patient survival (for OS), or of patient being free of disease recurrence (for TTR). Whenever a relevant event occurred (either death for OS, or disease recurrence for TTR), the curve drops. When a patient was lost to follow up without a relevant event occurring, a mark in the horizontal lines was made, indicating the last event-free time. P-values were obtained by comparing the decrease in patient population with and without the biomarkers.

The number of markers ultimately validated as described is relatively small, which may be attributable in part to the fact that the two patient populations are from different ethnic groups. Previous large samplings were collected in Chicago, Ill., USA and included a mix of Asian, Caucasian, African and Hispanic patients, while the validation samples were collected in Korea from a homogeneously Asian population. Additionally, the two samples sets were processed at different locations, Abbott Park for the first sample set and the Samsung Cancer Center for the second sample set. Although the sample processing in both locations followed the same suggested protocol, potential systems bias cannot be totally ruled out. Also, the two sample sets were assayed using different versions of Affymetrix SNPs arrays, between which density differed by a factor of eighteen (18). The additional probes included in the new array may reveal more detailed copy number variation events that were not observable using the older version of SNPs arrays.

TABLE 9

Validated genes within the identified biomarkers that correlate to clinical outcome of NSCLC patients

| GeneSymbol | Chromosome | Type | MarkerID | Event | Normal | PvalTTR | PvalOS |
|---|---|---|---|---|---|---|---|
| C11orf20 | chr11 | Amp | Marker10 | 6 | 67 | *0.0024* | *0.0477* |
| ESRRA | chr11 | Amp | Marker10 | 6 | 67 | *0.0024* | *0.0477* |
| HSPC152 | chr11 | Amp | Marker10 | 6 | 67 | *0.0024* | *0.0477* |
| KCNK4 | chr11 | Amp | Marker10 | 6 | 67 | *0.0024* | *0.0477* |
| PRDX5 | chr11 | Amp | Marker10 | 6 | 67 | *0.0024* | *0.0477* |
| GPR137 | chr11 | Amp | Marker10 | 5 | 68 | *0.0132* | 0.1138 |
| BAD | chr11 | Amp | Marker10 | 4 | 69 | *0.0232* | *0.0278* |
| DNAJC4 | chr11 | Amp | Marker10 | 4 | 69 | *0.0232* | *0.0278* |
| FKBP2 | chr11 | Amp | Marker10 | 4 | 69 | *0.0232* | *0.0278* |
| NUDT22 | chr11 | Amp | Marker10 | 4 | 69 | *0.0232* | *0.0278* |
| PLCB3 | chr11 | Amp | Marker10 | 4 | 69 | *0.0232* | *0.0278* |
| PPP1R14B | chr11 | Amp | Marker10 | 4 | 69 | *0.0232* | *0.0278* |
| TRPT1 | chr11 | Amp | Marker10 | 4 | 69 | *0.0232* | *0.0278* |
| VEGFB | chr11 | Amp | Marker10 | 4 | 69 | *0.0232* | *0.0278* |
| FLRT1 | chr11 | Amp | Marker10 | 4 | 69 | 0.1288 | *0.0069* |
| FADS2 | chr11 | Amp | Marker10 | 3 | 70 | 0.4208 | *0.0482* |
| FADS3 | chr11 | Amp | Marker10 | 3 | 70 | 0.4208 | *0.0482* |
| RAB3IL1 | chr11 | Amp | Marker10 | 3 | 70 | 0.4208 | *0.0482* |
| AKAP1 | chr17 | Amp | Marker11 | 3 | 70 | *0.0370* | 0.3782 |
| ANKFN1 | chr17 | Amp | Marker11 | 3 | 70 | *0.0370* | 0.3782 |
| C17orf67 | chr17 | Amp | Marker11 | 3 | 70 | *0.0370* | 0.3782 |
| COIL | chr17 | Amp | Marker11 | 3 | 70 | *0.0370* | 0.3782 |
| DGKE | chr17 | Amp | Marker11 | 3 | 70 | *0.0370* | 0.3782 |
| MSI2 | chr17 | Amp | Marker11 | 3 | 70 | *0.0370* | 0.3782 |
| MTVR2 | chr17 | Amp | Marker11 | 3 | 70 | *0.0370* | 0.3782 |
| NOG | chr17 | Amp | Marker11 | 3 | 70 | *0.0370* | 0.3782 |
| RNF126P1 | chr17 | Amp | Marker11 | 3 | 70 | *0.0370* | 0.3782 |
| SCPEP1 | chr17 | Amp | Marker11 | 3 | 70 | *0.0370* | 0.3782 |
| TRIM25 | chr17 | Amp | Marker11 | 3 | 70 | *0.0370* | 0.3782 |
| MYO15B | chr17 | Amp | Marker3 | 4 | 69 | *0.0312* | 0.1535 |
| SLC16A5 | chr17 | Amp | Marker3 | 4 | 69 | *0.0342* | 0.1126 |
| PACS1 | chr11 | Amp | Marker9 | 2 | 71 | *0.0015* | *0.0004* |
| DKFZp761E198 | chr11 | Amp | Marker9 | 4 | 69 | *0.0189* | *0.0136* |
| KAT5 | chr11 | Amp | Marker9 | 4 | 69 | *0.0189* | *0.0136* |
| LTBP3 | chr11 | Amp | Marker9 | 4 | 69 | *0.0189* | *0.0136* |
| MALAT1 | chr11 | Amp | Marker9 | 4 | 69 | *0.0189* | *0.0136* |
| RELA | chr11 | Amp | Marker9 | 4 | 69 | *0.0189* | *0.0136* |
| RNASEH2C | chr11 | Amp | Marker9 | 4 | 69 | *0.0189* | *0.0136* |
| SCYL1 | chr11 | Amp | Marker9 | 4 | 69 | *0.0189* | *0.0136* |
| EHBP1L1 | chr11 | Amp | Marker9 | 5 | 68 | *0.0224* | *0.0004* |
| FAM89B | chr11 | Amp | Marker9 | 5 | 68 | *0.0224* | *0.0004* |
| KCNK7 | chr11 | Amp | Marker9 | 5 | 68 | *0.0224* | *0.0004* |
| MAP3K11 | chr11 | Amp | Marker9 | 5 | 68 | *0.0224* | *0.0004* |
| PCNXL3 | chr11 | Amp | Marker9 | 5 | 68 | *0.0224* | *0.0004* |
| SIPA1 | chr11 | Amp | Marker9 | 5 | 68 | *0.0224* | *0.0004* |
| SSSCA1 | chr11 | Amp | Marker9 | 5 | 68 | *0.0224* | *0.0004* |
| CCNB1 | chr5 | Del | DelMarker27 | 19 | 54 | 0.3161 | *0.0495* |
| SLC30A5 | chr5 | Del | DelMarker27 | 19 | 54 | 0.3161 | *0.0495* |
| ARSK | chr5 | Del | DelMarker6 | 9 | 64 | *0.0033* | *0.0135* |
| FAM81B | chr5 | Del | DelMarker6 | 9 | 64 | *0.0033* | *0.0135* |
| GPR150 | chr5 | Del | DelMarker6 | 9 | 64 | *0.0033* | *0.0135* |
| MCTP1 | chr5 | Del | DelMarker6 | 10 | 63 | *0.0114* | *0.0051* |
| C5orf27 | chr5 | Del | DelMarker6 | 10 | 63 | *0.0122* | *0.0406* |
| CAST | chr5 | Del | DelMarker6 | 10 | 63 | *0.0122* | *0.0406* |
| GLRX | chr5 | Del | DelMarker6 | 10 | 63 | *0.0122* | *0.0406* |
| PCSK1 | chr5 | Del | DelMarker6 | 10 | 63 | *0.0122* | *0.0406* |
| RFESD | chr5 | Del | DelMarker6 | 10 | 63 | *0.0122* | *0.0406* |
| RHOBTB3 | chr5 | Del | DelMarker6 | 10 | 63 | *0.0122* | *0.0406* |
| SPATA9 | chr5 | Del | DelMarker6 | 10 | 63 | *0.0122* | *0.0406* |
| TTC37 | chr5 | Del | DelMarker6 | 10 | 63 | *0.0193* | *0.0491* |
| ELL2 | chr5 | Del | DelMarker6 | 11 | 62 | *0.0467* | 0.1066 |

Example 3

Figure 2:
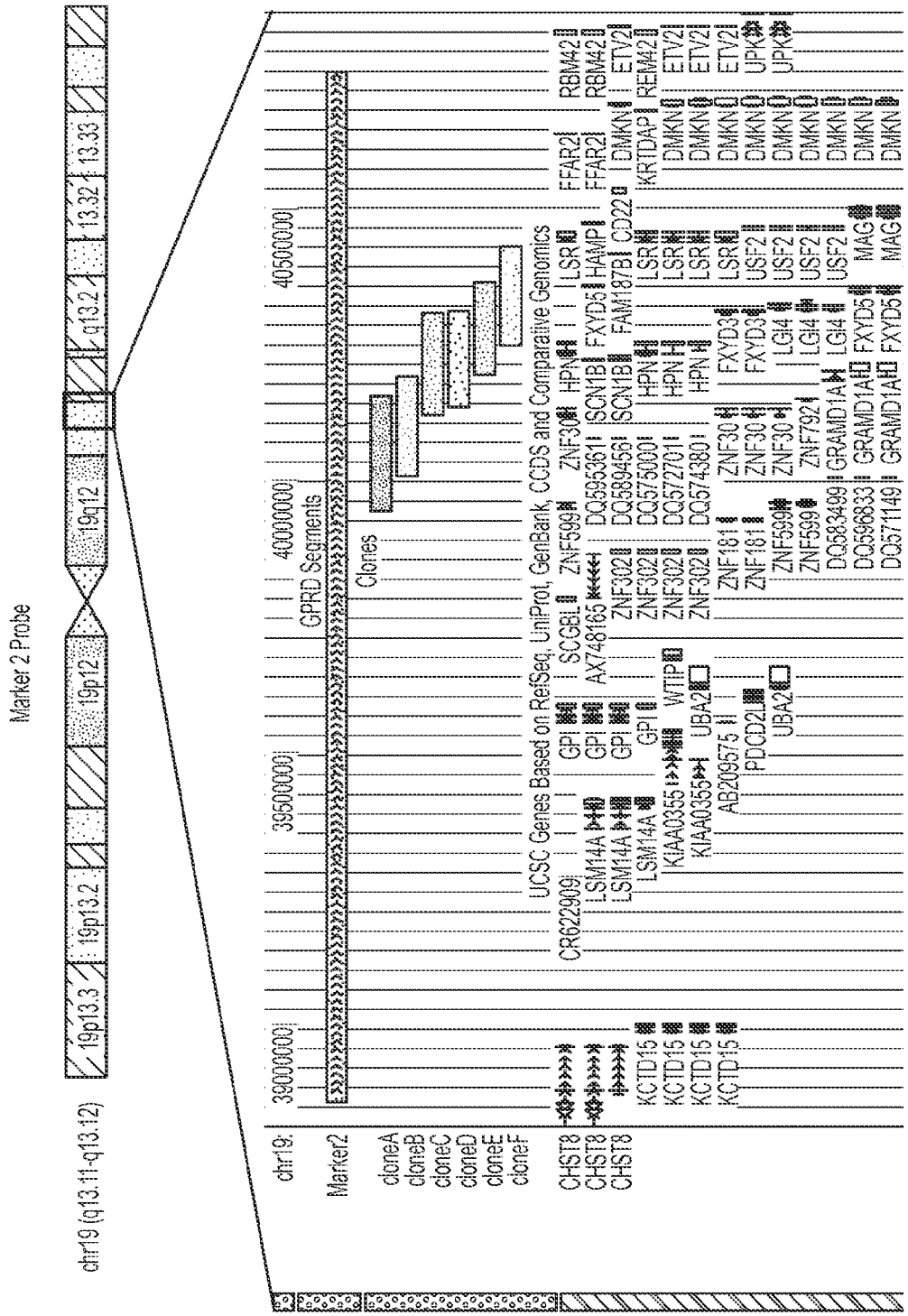
FIG. 2 a chromosomal map of a probe to "marker 2" on Chr19, at 19q13.11-q13.12.
Figure 3:
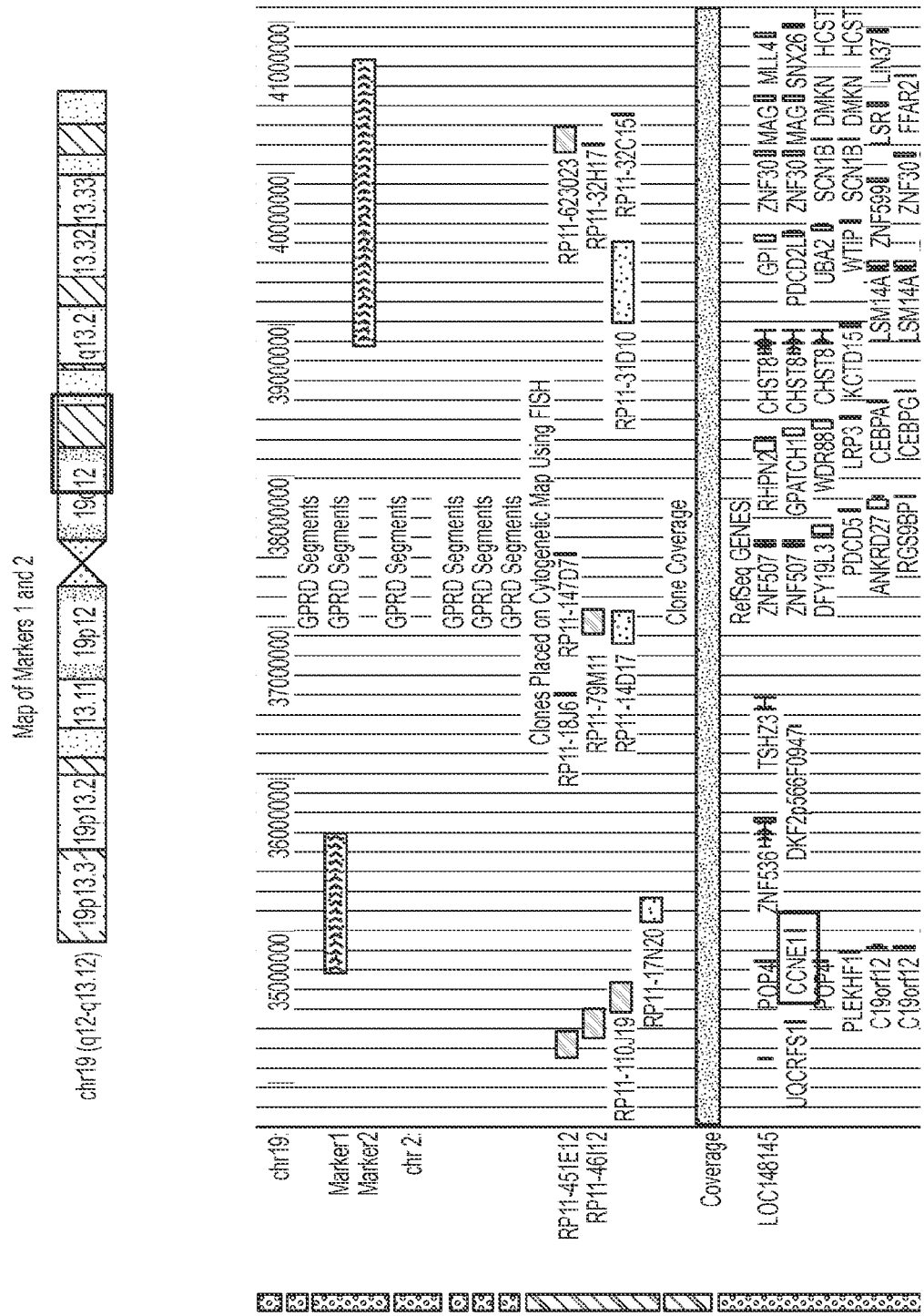
FIG. 3 is a chromosomal map of the probes to markers 1 and 2 on Chr19, at 19q12-13.12.
Figure 4:
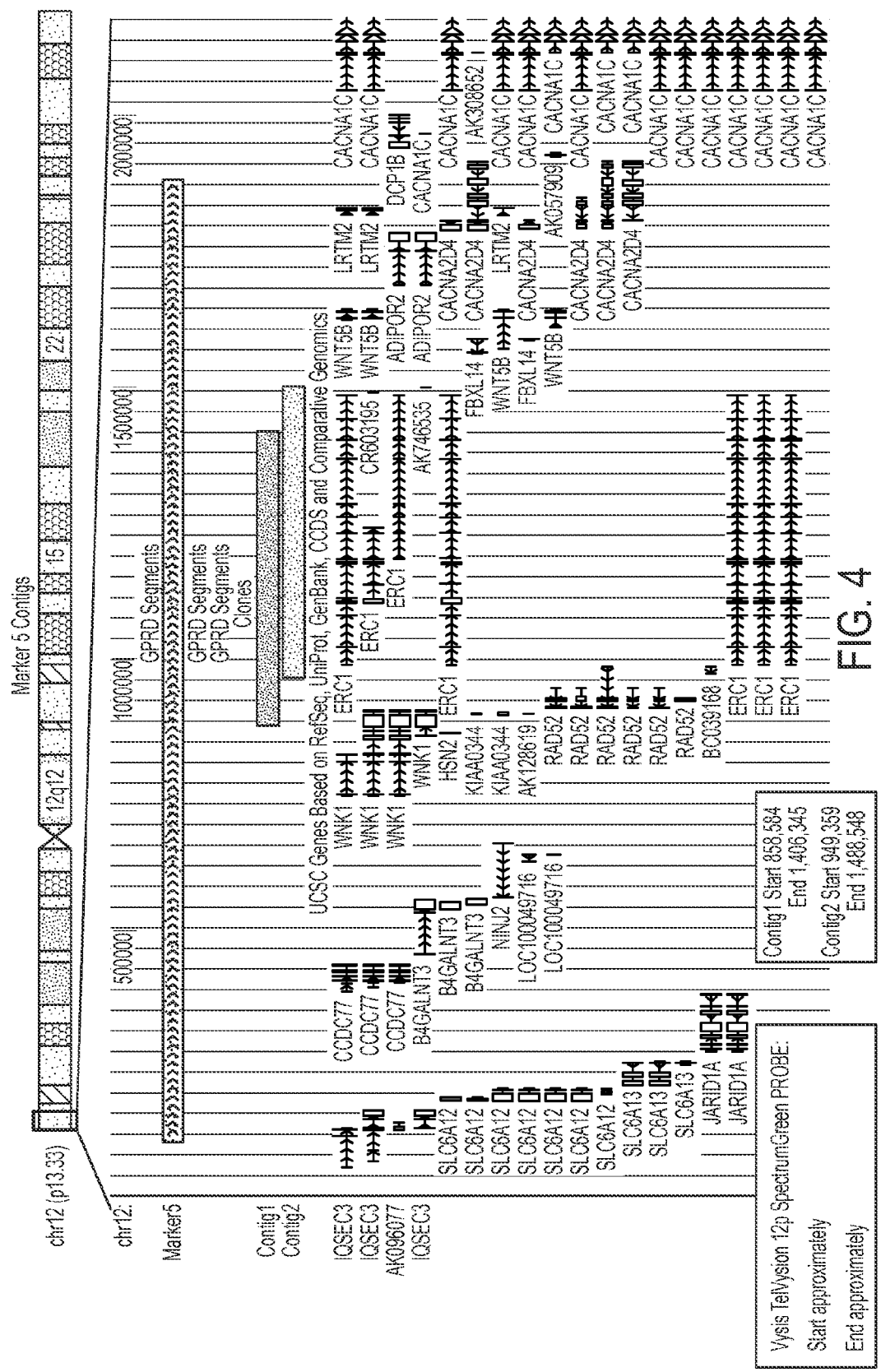
FIG. 4 is a chromosomal map of two contigs to "marker 5" on Chr12, at 12p13.33.
Figure 5:
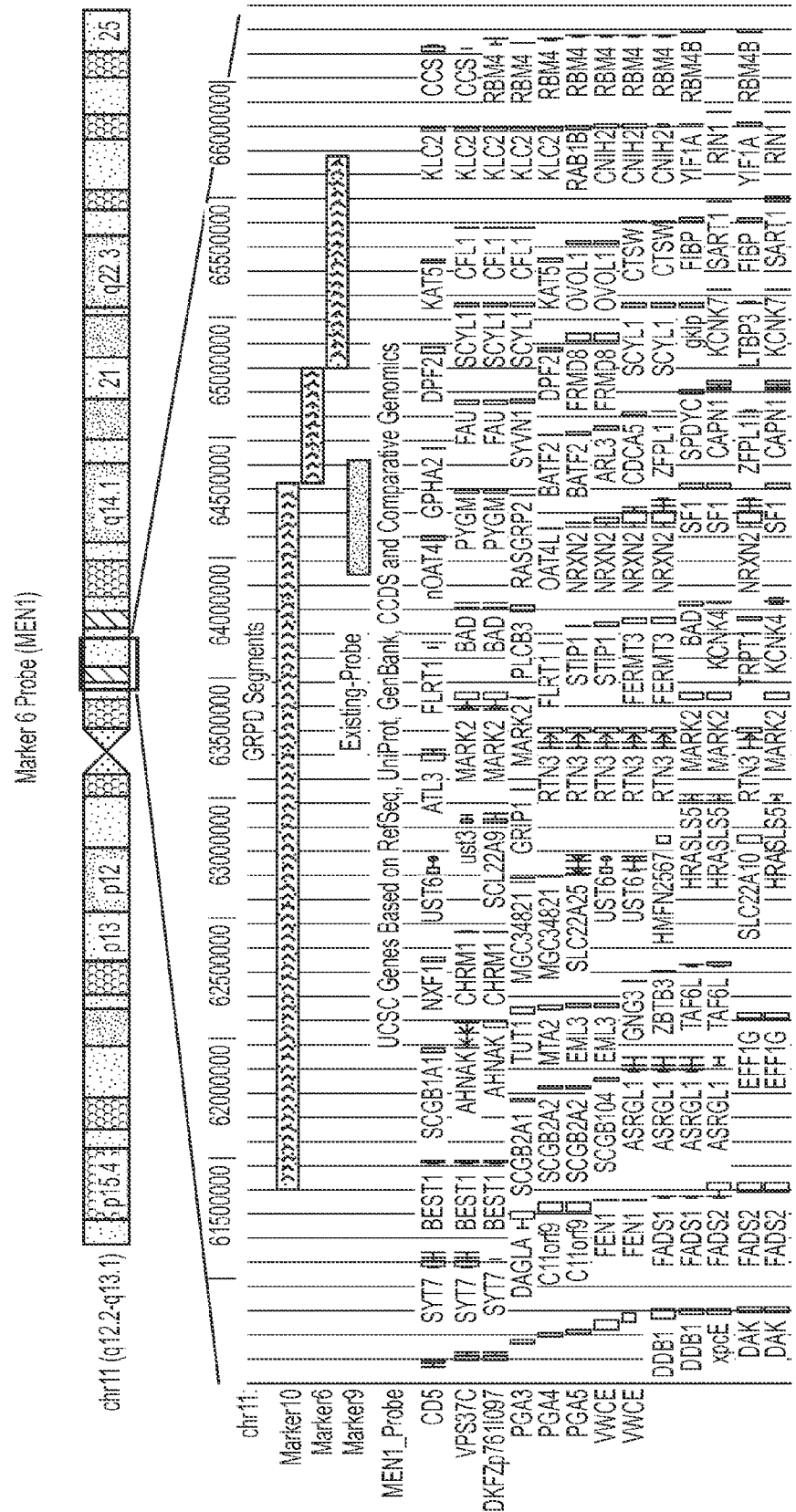
FIG. 5 is a chromosomal map of a probe to "marker 6" (MEN1) on Chr11, at 11q12.2-q13.1.
Figure 6:
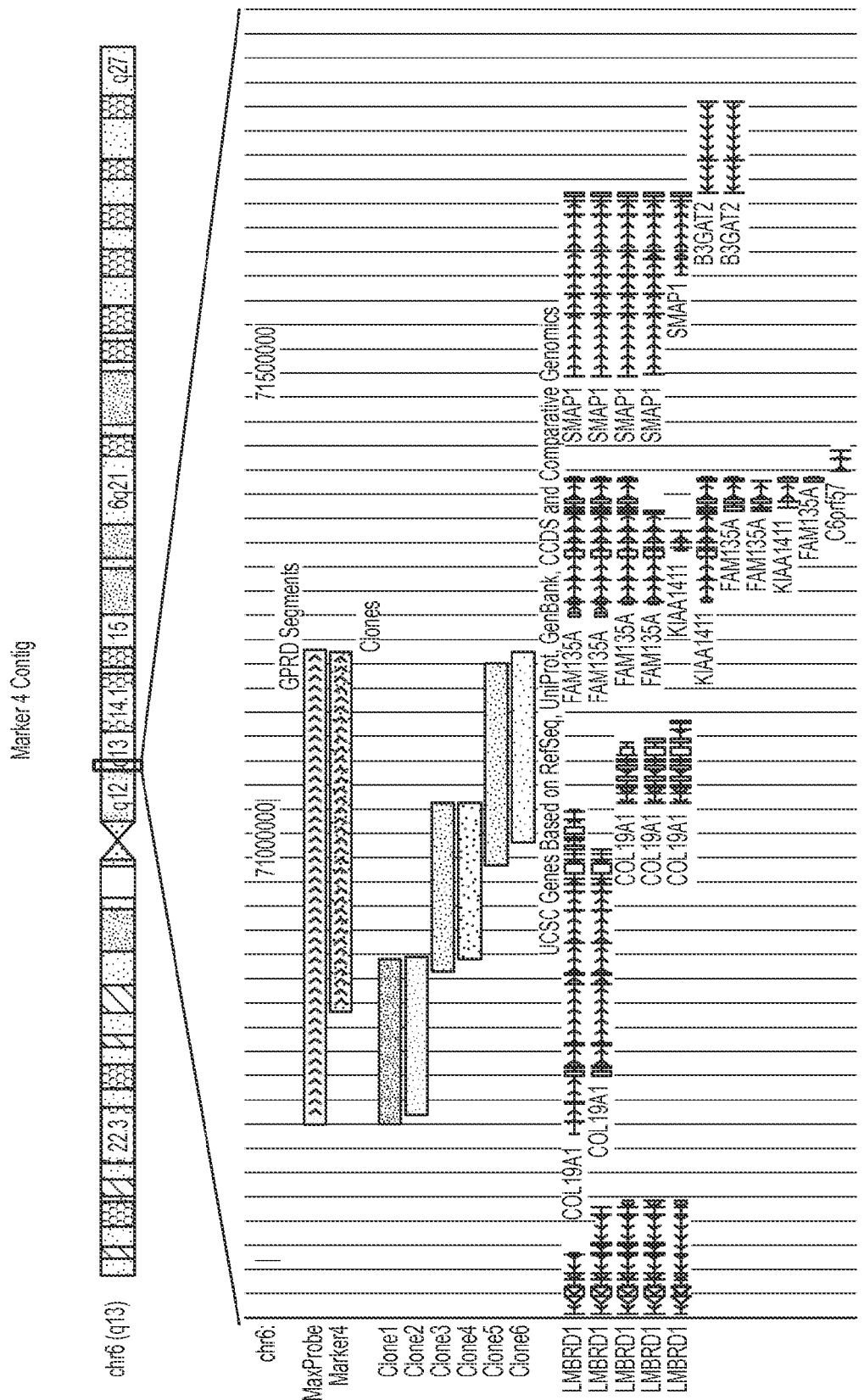
FIG. 6 is a chromosomal map of a probe to "marker 4" on Chr6, at 6q13.

FISH Probes To Chromosome Regions Associated with Increased Risk of Poor Disease Outcome in NSCLC Following identification and validation of the biomarkers as described in Examples 1 and 2 above, FISH probes to the identified chromosome regions, i.e., 1p, 2q, 3q, 3q, 4p, 4q, 5q, 6p, 6q, 8p, 9p, 10q, 11q, 12p, 14q, 16q, 17q, and 19q, were made at Abbott Molecular using standard techniques, each probe targeting a chromosome region or subregion as identified herein. Table lists the targeted chromosomal regions by chromosome, start and end positions, start and end bands, and marker type (Amp=gain, Del=loss). FIGS. 1-6 are chromosomal maps of selected FISH probes. FIG. 1 shows the mapping of a FISH probe to "marker 1" on Chr19, at 19q12. FIG. 2 shows the mapping of a FISH probe to "marker 2" on Chr19, at 19q13.11-g13.12. FIG. 3 maps the two probes shown in FIGS. 1 and 2 together, on Chr19, at 19g12-13.12. FIG. 4 shows the mapping of two FISH contigs to "marker 5" on Chr12, at 12p13.33. FIG. 5 shows the mapping of a FISH probe to "marker 6" (including MEN1) on Chr11, at 11q12.2-g13.1. FIG. 6 shows the mapping of a FISH probe to "marker 4" on Chr6, at 6q13. FISH probes were likewise generated to all amplification Markers 1-20 and deletion markers ("DelMarkers") 1-26.

TABLE 10

FISH probe targets

| chr | start.pos | end.pos | Start Band | End Band | Type | MarkerID |
|---|---|---|---|---|---|---|
| chr1 | 109538586 | 111118652 | p13.3 | p13.3 | Amp | Marker20 |
| chr2 | 147604021 | 151117679 | q22.3 | q23.3 | Amp | Marker13 |
| chr2 | 159911944 | 161423883 | q24.2 | q24.2 | Amp | Marker16 |
| chr2 | 200924525 | 204245414 | q33.1 | q33.2 | Amp | Marker17 |
| chr2 | 205893481 | 208053624 | q33.3 | q33.3 | Amp | Marker19 |
| chr2 | 213677020 | 214308243 | q34 | q34 | Del | DelMarker18 |
| chr3 | 97988751 | 98257089 | q11.2 | q11.2 | Del | DelMarker21 |
| chr3 | 119993321 | 121112610 | q13.32 | q13.33 | Del | DelMarker14 |
| chr4 | 43689020 | 44161565 | p13 | p13 | Del | DelMarker12 |
| chr4 | 44161566 | 44606114 | p13 | p13 | Del | DelMarker17 |
| chr4 | 46246303 | 47955581 | p12 | p12 | Del | DelMarker15 |
| chr4 | 81371219 | 83187388 | q21.21 | q21.22 | Del | DelMarker24 |
| chr4 | 105818261 | 107238628 | q24 | q24 | Del | DelMarker2 |
| chr5 | 50706878 | 52008065 | q11.2 | q11.2 | Del | DelMarker5 |
| chr5 | 53264432 | 53790965 | q11.2 | q11.2 | Del | DelMarker3 |
| chr5 | 55221121 | 58648144 | q11.2 | q11.2 | Del | DelMarker26 |
| chr5 | 60797829 | 62942846 | q12.1 | q12.1 | Del | DelMarker13 |
| chr5 | 62942847 | 67798156 | q12.1 | q13.1 | Del | DelMarker7 |
| chr5 | 67798156 | 68516077 | q13.1 | q13.2 | Del | DelMarker27 |
| chr5 | 94204208 | 96112445 | q15 | q15 | Del | DelMarker6 |
| chr6 | 36255222 | 36678343 | p21.31 | p21.31 | Amp | Marker18 |
| chr6 | 39088059 | 39850364 | p21.2 | p21.2 | Amp | Marker8 |
| chr6 | 70761833 | 71144537 | q13 | q13 | Amp | Marker4 |
| chr6 | 123724457 | 135574976 | q22.31 | q23.3 | Amp | Marker14 |
| chr8 | 6895465 | 8784654 | p23.1 | p23.1 | Amp | Marker15 |
| chr9 | 28057491 | 28114180 | p35.3 | p35.3 | Del | DelMarker11 |
| chr9 | 36056899 | 36988415 | p13.3 | p13.2 | Del | DelMarker1 |
| chr10 | 51929419 | 54199330 | q11.23 | q21.1 | Del | DelMarker25 |
| chr11 | 61374252 | 64310153 | q12.2 | q13.1 | Amp | Marker10 |
| chr11 | 64310154 | 64803976 | q13.1 | q13.1 | Amp | Marker6 |
| chr11 | 64803977 | 65684917 | q13.1 | q13.1 | Amp | Marker9 |
| chr12 | 93683 | 1867988 | p13.33 | p13.33 | Amp | Marker5 |
| chr14 | 27646449 | 28630571 | q12 | q12 | Del | DelMarker20 |
| chr14 | 38939630 | 40021400 | q21.1 | q21.1 | Del | DelMarker16 |
| chr14 | 43899026 | 46591909 | q21.3 | q21.3 | Del | DelMarker19 |
| chr14 | 48734855 | 51108156 | q22.1 | q22.1 | Del | DelMarker23 |
| chr14 | 51108156 | 52752331 | q22.1 | q22.2 | Del | DelMarker9 |
| chr14 | 55249852 | 60045332 | q22.3 | q23.1 | Del | DelMarker22 |
| chr14 | 61456273 | 68632720 | q23.2 | q24.1 | Del | DelMarker10 |
| chr16 | 45791880 | 46313827 | q12.1 | q12.1 | Del | DelMarker4 |
| chr17 | 43477124 | 44932837 | q21.32 | q21.33 | Amp | Marker12 |
| chr17 | 51532820 | 53211048 | q22 | q22 | Amp | Marker11 |
| chr17 | 69173224 | 71304619 | q25.1 | q25.1 | Amp | Marker3 |
| chr19 | 34722418 | 35643933 | q12 | q12 | Amp | Marker1 |
| chr19 | 38853838 | 40749461 | q13.11 | q13.12 | Amp | Marker2 |
| chr19 | 57033283 | 62189738 | q13.33 | q13.43 | Amp | Marker7 |

It is to be understood that the foregoing description is intended to illustrate and not limit the scope of the invention. Other aspects, advantages, and modifications of the invention are within the intended scope of the claims set forth below.

What is claimed is:

1. A method of predicting disease outcome in a patient being treated for lung cancer, from a biological sample from the patient, the method comprising:

contacting the sample with two or more fluorescent probes, each fluorescent probe targeting a different chromosome subregion, wherein the chromosome subregion is selected from the group consisting of: 1p13.3, 11q13.1, 17q25.1, 2q24.2, 2q33.3, 6p21.2, and 12p13.3;

incubating the two or more fluorescent probes with the sample under conditions in which each fluorescent probe binds selectively with a polynucleotide sequence on its target chromosomal subregion to form a stable hybridization complex;

detecting hybridization of the two or more fluorescent probes, wherein a hybridization pattern showing at least one gain at a chromosomal subregion targeted by the fluorescent probes is indicative of increased risk of poor disease outcome in the patient when compared to a baseline measure of disease outcome in patients having no gain at the two or more chromosomal subregions targeted by the two or more fluorescent probes; and administering a therapy to the patient that is indicated as having increased risk of poor disease outcome, wherein the patient that is indicated as having increased risk of poor disease outcome is treated post-resection with adjuvant chemotherapy or treated before the resection using neoadjuvant chemotherapy, wherein the biological sample comprises a tumor sample, wherein the cancer is stage I-II non-small cell lung cancer (NSCLC), and wherein the method is carried out by fluorescence in situ hybridization (FISH) with a fluorescent microscope or flow cytometer.

2. The method of claim 1, wherein a hybridization pattern showing a gain in 1p13.3 and 11q13.1 is indicative of poor disease outcome in the patient.

3. The method of claim 1, wherein the sample is contacted with a combination of at least three fluorescent probes, each fluorescent probe targeting a different chromosome subregion, wherein a hybridization pattern showing a gain in one or more of the chromosome subregions is indicative of poor disease outcome in the patient.

4. The method of claim 1, wherein the sample is contacted with a combination of at least four fluorescent probes, each fluorescent probe targeting a different chromosome subregion, wherein a hybridization pattern showing a gain in one or more of these chromosome subregions is indicative of poor disease outcome in the patient.

5. The method of claim 1 wherein the fluorescent probe combination distinguishes samples comprising stage I-II NSCLC at increased risk of poor disease outcome from samples that do not comprise stage I-II NSCLC at increased risk of poor disease outcome with a sensitivity of at least 93% and a specificity of at least 90%, wherein the sensitivity and specificity is determined using p-values obtained by comparing a decrease in overall survival or in time to recurrence in a patient population with and without the fluorescent probes.

6. The method of claim 5, wherein the sensitivity is at least 95% and the specificity is at least 90.4%.

7. The method of claim 5, wherein the sensitivity is at least 96% and the specificity is at least 91%.

8. The method of claim 1, wherein the probe combination comprises four probes.

9. The method of claim 1, wherein each fluorescent probe in the fluorescent probe combination is labeled with a different fluorophore.

10. The method of claim 1, wherein the sample comprises a lung biopsy specimen.

11. The method of claim 1, wherein each fluorescent probe targets a chromosome subregion selected from the group consisting of Chr 1, 109.5 Mb-111.1 Mb; Chr 11, 64.3 Mb-64.8 Mb; Chr 11, 64.8 Mb-65.7 Mb; Chr 17, 69.2 Mb-71.3 Mb; Chr 2, 159.9 Mb-161.4 Mb; Chr 2, 205.9 Mb-208.1 Mb; Chr 6, 39.1 Mb-39.9 Mb; and Chr 12, 93.7 kb-1.9 Mb.

* * * * *